(12) United States Patent
Dimarchi et al.

(10) Patent No.: US 8,669,228 B2
(45) Date of Patent: Mar. 11, 2014

(54) GLUCAGON ANALOGS EXHIBITING ENHANCED SOLUBILITY IN PHYSIOLOGICAL PH BUFFERS

(75) Inventors: Richard D. Dimarchi, Carmel, IN (US); Maria Dimarchi, Carmel, IN (US); Joseph Chabenne, Fishers, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 494 days.

(21) Appl. No.: 12/522,129

(22) PCT Filed: Jan. 3, 2008

(86) PCT No.: PCT/US2008/050099
§ 371 (c)(1),
(2), (4) Date: Jul. 2, 2009

(87) PCT Pub. No.: WO2008/086086
PCT Pub. Date: Jul. 17, 2008

(65) Prior Publication Data
US 2010/0190699 A1    Jul. 29, 2010

Related U.S. Application Data

(60) Provisional application No. 60/878,919, filed on Jan. 5, 2007.

(51) Int. Cl.
A61K 38/26 (2006.01)
C07K 14/605 (2006.01)

(52) U.S. Cl.
USPC .......................................... 514/7.2; 530/308

(58) Field of Classification Search
None
See application file for complete search history.

(56) References Cited

U.S. PATENT DOCUMENTS

| | | | |
|---|---|---|---|
| 4,275,152 A | 6/1981 | Esders et al. |
| 5,359,030 A | 10/1994 | Ekwuribe |
| 5,510,459 A | 4/1996 | Smith et al. |
| 5,512,549 A | 4/1996 | Chen et al. |
| 5,665,705 A | 9/1997 | Merrifield et al. |
| 5,783,674 A | 7/1998 | Geysin |
| 6,191,102 B1 | 2/2001 | DiMarchi et al. |
| 6,583,111 B1 | 6/2003 | DiMarchi et al. |
| 6,677,136 B2 | 1/2004 | Marshall et al. |
| 7,192,922 B2 | 3/2007 | Shannon et al. |
| 7,211,557 B2 | 5/2007 | DiMarchi et al. |
| 7,576,059 B2 | 8/2009 | Jonassen et al. |
| 2003/0021795 A1 | 1/2003 | Houston et al. |
| 2003/0143183 A1 | 7/2003 | Knudsen et al. |
| 2003/0204063 A1 | 10/2003 | Gravel et al. |
| 2004/0002468 A1 | 1/2004 | Wadsworth et al. |
| 2004/0235710 A1 | 11/2004 | DeFelippis et al. |
| 2005/0070469 A1 | 3/2005 | Bloom et al. |
| 2005/0095679 A1 | 5/2005 | Prescott et al. |
| 2005/0124550 A1 | 6/2005 | Peri |
| 2005/0153890 A1 | 7/2005 | Pan et al. |
| 2005/0288248 A1 | 12/2005 | Pan et al. |
| 2006/0003417 A1 | 1/2006 | Pan et al. |
| 2006/0003935 A1 | 1/2006 | Pan et al. |
| 2006/0171920 A1 | 8/2006 | Shechter et al. |
| 2006/0210534 A1 | 9/2006 | Lee et al. |
| 2006/0252916 A1 | 11/2006 | DiMarchi et al. |
| 2006/0286129 A1 | 12/2006 | Sarubbi |
| 2007/0042956 A1 | 2/2007 | Johansen et al. |
| 2007/0173452 A1 | 7/2007 | DiMarchi et al. |
| 2007/0203058 A1 | 8/2007 | Lau et al. |
| 2007/0287670 A1 | 12/2007 | Natarajan et al. |
| 2008/0113905 A1 | 5/2008 | DiMarchi et al. |
| 2008/0125574 A1 | 5/2008 | Sheffer et al. |
| 2008/0318837 A1 | 12/2008 | Quay et al. |
| 2009/0036364 A1 | 2/2009 | Levy et al. |
| 2009/0054305 A1 | 2/2009 | Schlein et al. |
| 2009/0062192 A1 | 3/2009 | Christensen et al. |
| 2009/0074769 A1 | 3/2009 | Glaesner et al. |
| 2009/0137456 A1 | 5/2009 | DiMarchi et al. |
| 2009/0192072 A1 | 7/2009 | Pillutla et al. |
| 2010/0190699 A1 | 7/2010 | DiMarchi et al. |
| 2010/0190701 A1 | 7/2010 | Day et al. |
| 2011/0065633 A1 | 3/2011 | DiMarchi et al. |
| 2011/0098217 A1 | 4/2011 | DiMarchi et al. |
| 2011/0166062 A1 | 7/2011 | DiMarchi et al. |
| 2011/0190200 A1 | 8/2011 | DiMarchi et al. |
| 2011/0257092 A1 | 10/2011 | DiMarchi et al. |
| 2011/0288003 A1 | 11/2011 | DiMarchi et al. |

FOREIGN PATENT DOCUMENTS

| | | |
|---|---|---|
| CA | 2024855 | 3/1992 |
| EP | 0220958 | 5/1987 |
| EP | 0479210 | 4/1992 |

(Continued)

OTHER PUBLICATIONS

De, et al., "Investigation of the feasibility of an amide-based prodrug under physiological conditions," Int. J. Pept. Res. Ther., 14, pp. 255-262 (2008).

(Continued)

*Primary Examiner* — Christine J Saoud

(74) *Attorney, Agent, or Firm* — Barnes & Thornburg LLP

(57) ABSTRACT

Modified glucagon peptides are disclosed having improved solubility while retaining glucagon agonist activity. The glycogen peptides have been modified by substitution of native amino acids with, and/or addition of, charged amino acids to the carboxy terminus of the peptide. The modified glucagon agonists can be further modified by pegylation, or the addition of a carboxy terminal peptide selected from the group consisting of SEQ ID NO: 20, SEQ ID NO: 21, SEQ ID NO: 23, or both to further enhance the solubility of the glucagon agonist analogs.

18 Claims, 10 Drawing Sheets

(56) References Cited

FOREIGN PATENT DOCUMENTS

| | | |
|---|---|---|
| EP | 0815135 | 9/1996 |
| EP | 1695983 B1 | 8/2006 |
| EP | 2036539 A1 | 3/2009 |
| EP | 2036923 A1 | 3/2009 |
| EP | 2398483 | 8/2010 |
| EP | 2300035 | 1/2012 |
| WO | WO96/29342 | 9/1996 |
| WO | WO 9707814 | 3/1997 |
| WO | 97/29180 | 8/1997 |
| WO | 98/11126 | 3/1998 |
| WO | 98/19698 | 5/1998 |
| WO | WO 9824464 | 6/1998 |
| WO | WO 9946283 | 9/1999 |
| WO | WO 0020592 | 4/2000 |
| WO | WO00/42026 | 7/2000 |
| WO | WO 0058360 | 10/2000 |
| WO | 01/083527 | 11/2001 |
| WO | WO 0181919 | 11/2001 |
| WO | 01/98331 | 12/2001 |
| WO | WO 0210195 | 2/2002 |
| WO | WO0213801 | 2/2002 |
| WO | 02/48183 | 6/2002 |
| WO | WO 02100390 | 12/2002 |
| WO | WO03/011892 | 2/2003 |
| WO | 03/020201 | 3/2003 |
| WO | WO03022304 | 3/2003 |
| WO | WO 03026635 | 4/2003 |
| WO | 03/035099 | 5/2003 |
| WO | WO 03082898 | 10/2003 |
| WO | 03/103572 | 12/2003 |
| WO | WO 03103697 | 12/2003 |
| WO | WO 03105760 | 12/2003 |
| WO | WO04000354 | 12/2003 |
| WO | WO 2004/022004 | 3/2004 |
| WO | 2004/067548 | 8/2004 |
| WO | WO 2004078777 | 9/2004 |
| WO | 2004/093823 | 11/2004 |
| WO | WO 2004/105781 | 12/2004 |
| WO | WO 2004/105781 A | 12/2004 |
| WO | WO 2004/105790 | 12/2004 |
| WO | WO 2004/105790 A | 12/2004 |
| WO | WO 2004103390 | 12/2004 |
| WO | WO 2005082928 | 9/2005 |
| WO | WO 2006086769 | 8/2006 |
| WO | WO 2006121904 | 11/2006 |
| WO | WO2006124529 | 11/2006 |
| WO | WO2006134340 A2 | 12/2006 |
| WO | WO 2007/022123 | 2/2007 |
| WO | WO 2007/022123 A | 2/2007 |
| WO | WO 2007028632 | 3/2007 |
| WO | WO2007028633 | 3/2007 |
| WO | 2007/056362 | 5/2007 |
| WO | 2007/100535 | 9/2007 |
| WO | WO 2007109354 | 9/2007 |
| WO | WO 2008021560 | 2/2008 |
| WO | WO 2008022015 | 2/2008 |
| WO | WO2008023050 | 2/2008 |
| WO | WO 2008076933 | 6/2008 |
| WO | 2008/086086 | 7/2008 |
| WO | 2008/101017 | 8/2008 |
| WO | WO2009030738 A1 | 3/2009 |
| WO | WO2009030774 A1 | 3/2009 |
| WO | WO2009034117 A1 | 3/2009 |
| WO | WO2009034118 A1 | 3/2009 |
| WO | WO2009034119 A1 | 3/2009 |
| WO | WO2009035540 A2 | 3/2009 |
| WO | 2009/058662 | 5/2009 |
| WO | 2009/058734 | 5/2009 |
| WO | WO2009/058734 | 5/2009 |
| WO | 2009/095479 | 8/2009 |
| WO | WO/2009/099763 | 8/2009 |
| WO | 2009/155257 | 12/2009 |
| WO | 2009/155258 | 12/2009 |
| WO | 2010/011439 | 1/2010 |
| WO | 2010/071807 | 6/2010 |
| WO | 2010/080605 | 7/2010 |
| WO | 2010/096052 | 8/2010 |
| WO | 2010/148089 | 12/2010 |
| WO | 2011/075393 | 6/2011 |
| WO | WO 2011087671 | 7/2011 |
| WO | WO 2011087672 | 7/2011 |
| WO | 2011/094337 | 8/2011 |
| WO | WO2011119657 | 9/2011 |
| WO | WO2011143208 | 11/2011 |
| WO | WO2011143209 | 11/2011 |
| WO | WO2011163012 | 12/2011 |
| WO | WO2011163473 | 12/2011 |

OTHER PUBLICATIONS

Madsen, et al., "Structure-activity and protraction relationship of long-acting glucagon-like peptide-1 derivatives: Importance of fatty acid length, polarity, and bulkiness," J. Med. Chem., 50, pp. 6126-6132 (2007).

PCT International Search Report for PCT/US2011/041601 completed by the US Searching Authority on Nov. 10, 2011.

PCT International Search Report for PCT/US2008/050099 completed by the US Searching Authority on Sep. 1, 2008.

Joshi et al., "The Degradation Pathways of Glucagon in Acidic Solutions," *International Journal of Pharmaceutics*, 203 (2000), pp. 115-125.

Joshi et al., "The Estimation of Glutaminyl Deamidation and Aspartyl Cleavage Rates in Glucagon," *International Journal of Pharmaceutics*, 273 (2004), pp. 213-219.

Wynne et al., "Subcutaneous Oxyntomodulin Reduces Body Weight in Overweight and Obese Subjects," *Diabetes*, vol. 54, Aug. 2005, pp. 2390-2395.

Joshi et al, "Studies on the Mechanism of Aspartic Acid Cleavage and Glutamine Deamidation in the Acidic Degradation of Glucagon," *Journal of Pharmaceutical Sciences*, vol. 94, No. 9, Sep. 2005, pp. 1912-1927.

Stigsnaes et al., "Characterisation and Physical Stability of PEGylated Glucagon," *International Journal of Pharmaceutics*, 330 (2007), pp. 87-98.

Robberecht, P. et al., "Receptor Occupancy and Adenylate Cyclase Activation in Rat Liver and Heart Membranes by 10 Glucagon Analogs Modified in Position 2, 3, 4, 25, 27 and/or 29," Regulatory Peptides, 21 (1988), 117-128.

"Peptides: Frontiers of Peptide Science," Proceedings of the Fifteenth American Peptide Symposium, Jun. 14-19, 1997, Nashville, Tennessee, USA; ed. James P. Tam and Praven T.P. Kaumaya.

Ahn, J.M. et al., A new approach to search for the bioactive conformation of glucagon: positional cyclization scanning, *J. Med. Chem.*, 44(19): 3109-16, Sep. 13, 2001.

Ahn, J.M. et al., Development of potent truncated glucagon antagonists, *J. Med. Chem.*, 44(9): 1372-9, Apr. 26, 2001. (Abstract).

Chabenne et al., Optimization of the native glucagon sequence for medicinal purposes, J. Diabetes. Sci. Technol., 4(6): 1322-31, Nov. 1, 2010.

Day et al., Charge inversion at position 68 of the glucagon and glucagon-like peptide-1 receptors supports selectivity in hormone action. *J. Pept. Sci.*, 17(3): 218-25, Nov. 30, 2010.

De, Design of peptide-based prodrug chemistry and its application to glucagon-like Peptide 1. Masters Thesis Aug. 2007. [Retrieved from the Internet on Jun. 16, 2009: <https://scholarworksiu.edu/dspace/browse?value=De%2C+ArnabBtype=author>]; p. 8, para 2; p. 16, para 3; p. 40, para 1; p. 66, para 2; p. 77, para 1-2; p. 79, para 1.

Gelfanov, et al., Discover and Structural Optimization of High Affinity Co-Agonists at the Glucagon and GLP-1 Receptors, Understanding Biology Using Peptides, Springer, pp. 763-764, Jun. 23, 2005.

GenBank entry AAI5278. Jul. 15, 2006. [Retrieved from the Internet Jun. 18, 2009:~http://www._ncbi._nim.n ih.gov/protein/13528972>].

Habegger et al., The metabolic actions of glucagon revisited, *Nat. Rev. Endocrinol.*, 6(12): 689-97, Oct. 19, 2010.

Harris, J. Milton, Final Word: PEGylation—A "Sunset" Technology? <http://licence.icopyright.net/user/viewFreeUse.act?fuid=OTU1NjY3OA%3D%3D>, BioPharm International, Jun. 1, 2004.

(56) References Cited

OTHER PUBLICATIONS

Heppner et al., Glucagon regulation of energy metabolism, *Physiol Behav.*, 100(5): 545-8, Apr. 8, 2010.
Hruby et al., "The Design and Biological Activities of Glucagon Agonists and Antagonists, and Their Use in Examining the Mechanisms of Glucose Action," *Curr. Med. Chem.-Imm., Endoc. & Metab. Agents*, 2001, 1, pp. 199-215.
Jonathan Day et al., "A New Glucagon and GLP-1 Co-Agonist Eliminates Obesity in Rodents," Nature Chemical Biology, vol. 5, No. 10, Oct. 2009, pp. 749-757.
Krstenansky et al., "Importance of the C-terminal α-helical structure for glucagon's biological activity," Int. J. Peptide Protein Res., 32, 1988, 468-475.
Lee et al., "Synthesis, Characterization, and Pharmacokinetic Studies of PEGylated Glucagon-like Peptide-1," *Bioconjugate Chem.*, 2005, vol. 16, No. 2, pp. 377-382.
Levy et al., Optimization of the C-terminal Sequence in Glucagon to Maximize Receptor Affinity, Poster Presentation, Jun. 19, 2005.
Levy et al., Optimization of the C-terminal Sequence in Glucagon to Maximize Receptor Affinity, *Understanding Biology Using Peptides*, American Peptide Society, Apr. 2006.
Li et al., Crystallization and preliminary X-ray analysis of anti-obesity peptide hormone oxyntomodulin, *Protein & Peptide Letters*, 15(2): 232-4 (2008).
Li et al., Design, synthesis and crystallization of a novel glucagon analog as a therapeutic agent, *Acta Crystallogr. Sect. F Struct. Biol. Cryst. Commun.*, 63(Pt 7):599-601, Jun. 15, 2007.
Li et al., Structural Basis for Enhanced Solublity of a C-Terminally Extended Glucagon Analog , *Biopolymers.*, 96(4): 480 (2011).
M.J. Roberts et al., "Chemistry for Peptide and Protein PEGylation," Advance Drug Delivery Reviews, Elsevier BV, Amsterdam, NL, vol. 54, No. 4, Jun. 17, 2002, pp. 459-476.
Marita P. Feldkaemper et al., "Localization and Regulation of Glucagon Receptors in the Chick Eye and Preproglucagon and Glucagon Receptor Expression in the Mouse Eye," Experimental Eye Research, Academic Press Ltd., London, vol. 79, No. 3, Sep. 1, 2004, pp. 321-329.
McKee et al., Receptor Binding and Adenylate Cyclase Activities of Glucagon Analogues Modified in the N-Terminal Region, Biochemistry, 25: 1650-6 (1986).
Nogueiras et al., Direct control of peripheral lipid deposition by CNS GLP-1 receptor signaling is mediated by the sympathetic nervous system and blunted in diet-induced obesity, J. Neurosci., 29(18): 5916-25, May 6, 2009.
Ouyang et al., Discovery of Bi-Functional Peptides Balanced in Glucagon Antagonism & GLP-1 Agonism. A Search for the Molecular Basis in the Inversion of Activity at Homologous Receptors, 71st Scientific sessions of American Diabetes Association 2011—Post-Conference Review and Analysis.
Pan et al., Design of a Long Acting Peptide Functioning as Both a Glucagon-like Peptide-1 Receptor Agonist and a Glucagon Receptor Agonist, *J. Biol. Chem.*, 281(18): 12506-15, Table 1, May 5, 2006.
Patterson et al., A novel human-based receptor antagonist of sustained action reveals body weight control by endogenous GLP-1, *ACS Chem Biol.*, 6(2): 135-45 Nov. 4, 2010.
Patterson et al., Functional association of the N-terminal residues with the central region in glucagon-related peptides, *J. Peptide Sci.*, First published online Jun. 10, 2011.
PCT International Search Report for PCT/US2008/053857 completed by the US Searching Authority on Sep. 16, 2008.
PCT International Search Report for PCT/US2008/080973 completed by the US Searching Authority on Jun. 6, 2009.
PCT International Search Report for PCT/US2008/081333 completed by the US Searching Authority on Mar. 12, 2009.
PCT International Search Report for PCT/US2009/031593 completed by the US Searching Authority on Jun. 18, 2009.
Sapse et al., The Role of Sale Bridge Formation in Glucagon: An Experimental and Theoretical Study of Glucagon Analogs and Peptide Fragments of Glucagon, *Molec. Med.*, 8(5): 251-62, May 1, 2002.

Traylor et al., Identification of the High Potency Glucagon Agonist with Enhanced Biophysical Stability and Aqueous Solubility, Poster Abstract PY 10, pp. 505-506, Jun. 10, 2005.
Trivedi, D. et al., Design and synthesis of conformationally constrained glucagon analogues, *J. Med. Chem.*, 43(9): 1714-22, May 4, 2000 (Abstract).
Tschoep et al., A Novel Glucagon/GLP-1 Co-Agonist Eliminates Obesity in Rodents, Diabetes, 58 (Supp. 1): A83 (2009).
Unson et al., "Glucagon antagonists: Contribution to binding and activity of the amino-terminal sequence 1-5, position 12 and the putative alpha-helical segment 19-27," J. Biol. Chem. v264, pp. 789-794, Jan. 15, 1989, p. 792, para 1, Table 1.
Unson et al., Positively Charged Residues at Positions 12, 17, and 18 of Glucagon Ensure Maximum Biological Potency, *J. Biol. Chem.*, 273(17): 10308-12 (1998).
Ward et al., In vitro and in vivo evaluation of native glucagon and glucagon analog (MAR-D28) during aging: lack of cytotoxicity and preservation of hyperglycemic effect, J. Diabetes Sci. Technol., 4(6):1311-21, Nov. 1, 2010.
Yang et al., Synthesis and Biological Assessment of Sulfonic Acid-Based Glucagon Antagonists, Understanding Biology Using Peptides, American Peptide Symposia, 9(Part 6): 305-6 (2006).
Zhang et al., Design and synthesis of novel GLP1 analogues with significantly prolonged time action, Biopolymers., 80(4): 555 (2005).
Azizeh et al., "Topographical amino acid substitution in position 10 of glucagon leads to antagonists/partial agonists with greater binding differences," J. Med. Chem., vol. 39, No. 13, Jun. 21, 1996, pp. 2449-2455.
Azizeh et al., "Pure glucagon antagonists: biological activities and cAMP accumulation using phosphodiesterase inhibitors," Peptides 1997, vol. 18, No. 5, pp. 633-641.
Phillips et al., "Supramolecular Protein Engineering: Design of Zinc-Stapled Insulin Hexamers as a Long Acting Depot," J. Biol. Chem., vol. 285, No. 16, Apr. 16, 2010, pp. 11755-11759.
Murphy, et al., "Potent Long-Acting Alkylated Analogs of Growth Hormone-Releasing Factor," Pept. Res., vol. 1. No. 1, pp. 36-41 (1988).
Perret et al., "Mutational analysis of the glucagon receptor: similarities with the vasoactive intestinal peptide (VIP)/pituitary adenylate cyclase-activating peptide (PACAP)/secretin receptors for recognition of the ligand's third residue," J. Biochem., 362 (2002), pp. 389-394.
Gysin et al., "Design and Synthesis of Glucagon Partial Agonists and Antagonists," Biochemistry, 25, (1986), pp. 8278-8284.
PCT International Search Report for PCT/US2009/047437 completed by the US Searching Authority on Nov. 3, 2009.
Supplemental European Search Report issued in connection with EP Application No. 09767567.2 issued on Jun. 17, 2011.
Extended EP Search Report completed by the EP Searching Authority on Apr. 6, 2011 in connection with EP Patent Application No. 08845852.6.
DatabaseEMBL, Jul. 16, 2007, Richard DiMarchi and David Smiley, "Human Glucagon Peptide SEQ ID No. 1," XP002631582, retrieved from EBI, Database Accession No. AGB07042, Abstract.
Day, J.; Patterson, J.; Gelfanov, V. and DiMarchi, Richard Molecular-basis for Specificity in Biological Action at the Homologous Glucagon and GLP-1 Receptors, (2009) Proceedings of the 21st American Peptide Society 142-143.
De, A. and DiMarchi, R. Synthesis & Analysis of Peptide Hormone-based prodrugs, (2009) Proceedings of the 21st American Peptide Society 160-161.
De, Arnab; DiMarchi, Richard D. Investigation of the feasibility of an amide-based prodrug under physiological conditions. International Journal of Peptide Research and Therapeutics (2008), 14(4), 393.
De, A. and DiMarchi, R. Synthesis & Characterization of Ester-Based Prodrugs of Glucagon-Like Peptide 1, Peptide Science (2010) 94(4) 448-456.
DiMarchi, Richard, "The Use of Bioproducts in the Treatments of Metabolic Diseases" presentation slides for the Keystone Symposia (Jan. 25, 2009, Banff, Alberta).

(56) References Cited

OTHER PUBLICATIONS

Finan, B.; Gelfanov, V. and DiMarchi, R. Assessment of a Tat-Derived Peptide as a Vector for Hormonal Transport, (2009) Proceedings of the 21st American Peptide Society 321-322.
Kukuch, A.; Patterson, J.; DiMarchi, R. and Tolbert, T Immunoglobulin Fc-based Peptide Fusion Proteins as a Basis for Optimizing In Vivo Pharmacology, (2009) Proceedings of the 21$^{st}$ American Peptide Society 177-178.
Ma, T.; Day, J.; Gelfanov, V. and DiMarchi, R. Discovery and Structural Optimization of High Affinity Co-Agonists at the Glucagon and GLP-1 Receptors, (2009) Proceedings of the 21$^{st}$ American Peptide Society 146-147.
Ouyang et al., "Synthesis and Characterization of Peptides with Glucagon Antagonism and GLP-1 Agonism," poster presentation at the 21$^{st}$ American Peptide Symposium (Jun. 7-12, 2009, Bloomington, IN).
Tschoep et al., "A Novel Glucagon/GLP-1 Co-Agonist Eliminates Obesity in Rodents," American Diabetes Association Abstract No. 313-OR (2009).
Tschoep, Matthias, "A Novel Glucagon/GLP-1 Co-Agonist Eliminates Obesity in Rodents" presentation slides for the 2009 American Diabetes Association meeting (Jun. 5-9, 2009, New Orleans, LA).
Tschoep, Matthias, "Afferent Gut Hormones in the Control of Energy Balance and Metabolism" presentation slides for the 21st American Peptide Symposium (Jun. 7-12, 2009, Bloomington, IN).
Ward, B.; Finan, B.; Gelfanov, V. and DiMarchi, R. Exploring the N-terminal Hydrophobic Faces of Glucagon and Glucagon-like Peptide-1, (2009) Proceedings of the 21$^{st}$ American Peptide Society 153-154.
Yang, B. and DiMarchi, R.D. (2005). A Novel Approach to Resin-based Cysteine Alkylation Peptides: Chemistry, Structure and Biology, Proceedings of the XIX American Peptide Symposium, (88-89).
Irwin et al., "Early administration of the glucose-dependent insulinotropic polypeptide receptor antagonist (Pro$^3$) GIP prevents the development of diabetes and related metabolic abnormalities associated with genetically inherited obesity in ob/ob mice," Diabetologia 50:1532-1540 (2007).
Kulkarni, "GIP: No Longer the Neglected Incretin Twin?," Science Translational Medicine 2(49): p. 47, Sep. 15, 2010.
Montrose-Rafizadeh et al., "High Potency Antagonists of the Pancreatic Glucagon-like Peptide-1 Receptor," Journal of Biological Chemistry, 272(34) 21201-21206 (1997).
Sturm et al., "Structure-Function Studies on Positions 17, 18, and 21 Replacement Analogues of Glucagon: The Importance of Charged Residues and Salt Bridges in Glucagon Biological Activity," J Med Chem 1998, 41, 2693-2700.
Habi et al., Peptide Science, vol. 80, Issue 4, pp. 608 and 579 (abstracts only).
Habi, "Special Issue: Program and Abstracts for the 19th American Peptide Symposium, 2005, Abstracts of Poster Section C," (pp. 574-603) Article first published online. Jun. 10, 2005 | DOI: 10.1002/bip.20325.
Blache et al., "Development of an oxyntomodulin/glicentin C-terminal radioimmunoassay using a "thiol-maleoyl" coupling method for preparing the immunogen," Anal Biochem 1988 173(1):151-159 (1988), abstract only.
Vijayalakshmi et al., "Comparison of Helix-Stabilizing Effects of α, α-dialkyl Glycines with Linear and Cycloalkyl Side Chains", Biopolymers 53: 84-98 (Jan. 21, 2000).
Andrews et al., "Forming Stable Helical Peptides Using Natural and Artificial Amino Acids", Tetrahedron 55: 11711-11743, (1999).
Battersby et al., "Diketopiperazine Formation and N-Terminal Degradation in Recombinant Human Growth Hormone", International Journal of Peptide & Protein Research 44: 215-222, (1994).
Eriksson et al., "hPEPT1 Affinity and Translocation of Selected Gln-Sar and Glu-Sar Dipeptide Derivatives", Molecular Pharmaceutics vol. 2, No. 3: 242-249 (May 10, 2005).
Garcia-Aparicio et al., "Design and Discovery of a Novel Dipeptidyl-peptidase IV (CD26)-Based Prodrug Approach", J. Med. Chem. 49: 5339-5351 (2006).
Goolcharran et al., "Comparison of the Rates of Deamidation, Diketopiperazine Formation, and Oxidation in Recombinant Human Vascular Endothelial Growth Factor and Model Peptides", AAPS Pharmsci 2000 2(1) article 5: 1-6 (Mar. 17, 2000).
Santos et al., Cyclization-Activated Prodrugs. Synthesis, Reactivity and Toxicity of Dipeptide Esters of Paracetamol, Bioorganic & Medicinal Chemistry Letters 15: 1595-1598 (2005).
Schafmeister et al., "An All-Hydrocarbon Cross-Linking System for Enhancing the Helicity and Metaboli Stability of Peptides", J. Am. Chem. Soc. 122: 5891-5892 (2000).
Walensky et al., "Activation of Apoptosis in Vivo by a Hydrocarbon-Stapled BH3 Helix", Science 205: 1466-1470 (Sep. 3, 2004).
Lebl, Michal, "Peptides: Breaking Away: The Proceedings of the Twenty-First American Peptide Symposium", Prompt Scientific Publishing (2009).
"Legacy Products—'Back to the Future'," presentation to Eli Lilly and Co., Sep. 22, 2005.
"Application of Chemical Biotechnology to Optimization of Endocrine Hormones," Carothers Lecture, Mar. 22, 2007.
"The Emergence of Chemical Biotechnology & Its Application to Optimization of Endocrine Hormones," UMBC presentation, Mar. 26, 2008.
"Emergence of Chemical Biotechnology," Eli Lilly and Co. presentation, Jun. 22, 2009.
"Novel Glucagon-Like Chimera Peptides—Virtues of Combinatorial Pharmacology," Keystone Conference, Apr. 12-17, 2010, Whistler, B.C.
"Novel Glucagon-Like Chimera Peptides—Virtues of Combinatorial Pharmacology," AAPS May 2010.
"Two for the Money" Gut Hormone Hybrids, Tschoep, ADA meeting, Jun. 25-29, 2010, Orlando, FL.
"Biotechnology—A Basis for Better Health & Economic Prosperity," Ohio State University presentation, Aug. 28, 2010.
"Novel Glucagon-Based Peptides—Virtues of Combinatorial Pharmacology," European Peptide Symposium, Sep. 5-9, 2010, Copenhagen, Denmark.
"Biotechnology—A Basis for Better Health & Economic Prosperity," Indiana University television presentation, Nov. 2010.
"Novel Glucagon-Based Peptides—Virtues of Combinatorial Pharmacology," University of Michigan, Oct. 13, 2010.
"Novel Glucagon-Based Peptides—Virtues of Combinatorial Pharmacology," Yale University, May 13, 2011.
"Speaking From the Gut: From Gastrointestinal Hormones to Combinatorial Therapies," Presentation to American Diabetes Association, Jun. 25, 2011.
"The Pursuit of Transformational Medicines," presentation to American Peptide Symposium, Jun. 25-30, 2011, San Diego, CA.
"The Pursuit of Transformational Medicines," NP2D presentation, Dec. 4, 2011.
"The Pursuit of Transformational Medicines," Keystone presentation, Jan. 29-Feb. 3, 2012, Santa Fe, NM.
"Novel Glucagon Peptides That Demonstrate the Virtues of Combinatorial Pharmacology," University of Toledo, Mar. 22, 2012.
Althage et al.,JBC "Targeted Ablation of GIP-Producing Cells in Transgenic mice reduces obesity and insulin resistance induced by a high fat diet" 2008).
Chia et al., "Exogenous glucose-dependent insulinotropic polypeptide worsens post-prandial hyperglycemia in type 2 diabetes," Diabetes, 58: 1342-1349 (2009).
Drucker, "Glucagon Gene Expression in Vertebrate Brain," The Journal of Biological Chemistry, vol. 263, No. 27, pp. 13475-13478, 1988.
Drucker, "The biology of incretin hormones," Cell Metabolism 3:153-165 (2006).
PCT International Search Report for PCT/US2009/034448 completed by the US Searching Authority on Jun. 4, 2010.
PCT International Search Report for PCT/US2009/068678 completed by the US Searching Authority on May 5, 2010.
Pan et al., "Synthesis of Cetuximab-Immunoliposomes via a Cholesterol-Based Membrane Anchor for Targeting of EGFR," Bioconjugate Chem., 18, pp. 101-108, 2007.
PCT International Search Report for PCT/US2009/047447 completed by the US Searching Authority on Mar. 19, 2010.

(56) References Cited

OTHER PUBLICATIONS

Collie et al., "Purification and sequence of rat oxyntomodulin," Proc. Natl. Acad. Sci. USA, vol. 91, pp. 9362-9366, Sep. 1994.

Sueiras-Diaz et al., "Structure-Activity Studies on the N-Terminal Region of Glucagon," J. Med. Chem., 27, pp. 310-315, 1984.

Hjorth et al., "glucagon and Glucagon-like Peptide 1: Selective Receptor Recognition via Distinct Peptide Epitopes," The Journal of Biological Chemistry, vol. 269, No. 48, pp. 30121-30124, Dec. 2, 1994.

Unson et al., "Role of Histidine-1 in Glucagon Action," Archives of Biochemistry and Biophysics, vol. 300, No. 2, pp. 747-750, Feb. 1, 1993.

Sato, H., "Enzymatic procedure for site-specific pegylation of proteins," Advanced Drug Delivery Reviews 54, pp. 487-504 (2002).

"Novel Glucagon-Like Chimera Peptides—Virtues of Combinatorial Pharmacology," University of Cincinnati, Jun. 2010.

"Molecular Miracles," Indiana University, Apr. 13, 2011.

"Novel Glucagon-Based Peptides—Virtues of Combinatorial Pharmacology," Aug. 31, 2011, Berlin.

Ward, "Fatty Acid Acylation of Peptides: Developing strategies to enhance medicines for treating metabolic disorders," Jan. 14, 2009.

DiMarchi, "Peptides—Development of Prodrug Chemistry," RBF Symposium Feb. 1-4, 2011 India.

Tschoep, "CNS Integration of Systems Metabolism: Target Opportunities for Diabetes Prevention and Therapy," RBF Symposium Feb. 1-4, 2011 India.

Yang et al., "Synthesis and Biological Assessment of Sulfonic Acid-Based Glucagon Antagonists," American Peptide Society, 2005.

Yang et al., "Synthesis and Biological Assessment of Sulfonic Acid-Based Glucagon Antagonists," poster presentation to American Peptide Society, 2005.

Yang et al., "A Novel Approach to Resin-Based Cysteine Alkylation," poster presentation to American Peptide Society, 2005.

PCT International Search Report for PCT/US2010/038825 completed by the US Searching Authority on Sep. 15, 2010.

PCT International Search Report for PCT/US2010/059724 completed by the US Searching Authority on Jun. 14, 2011.

Wibowo, Synthesis, Purification, and Biological Activity of AIB Substituted Glucagon and GLP-1 Peptide Analogues (2005-2006) vol. 45, 707=738, accessed https://scholarworks.iu.edu/dspce/handle/2022/326 on Jul. 17, 2012.

O'Brien, Assay for DPPIV Activity using Homogenous, Luminescent Method, Cell Notes 2005, 11:8-11.

Evans et al., "Effect of β-Endorphin C-Terminal Peptides on Glucose Uptake in Isolated Skeletal Muscles of the Mouse," Peptides, vol. 18, No. 1, pp. 165-167, (1997).

Hansen et al., "Incretin hormones and insulin sensitivity," Trends in Endocrinology and Metabolism, vol. 16, No. 4, May/Jun. 2005, pp. 135-136.

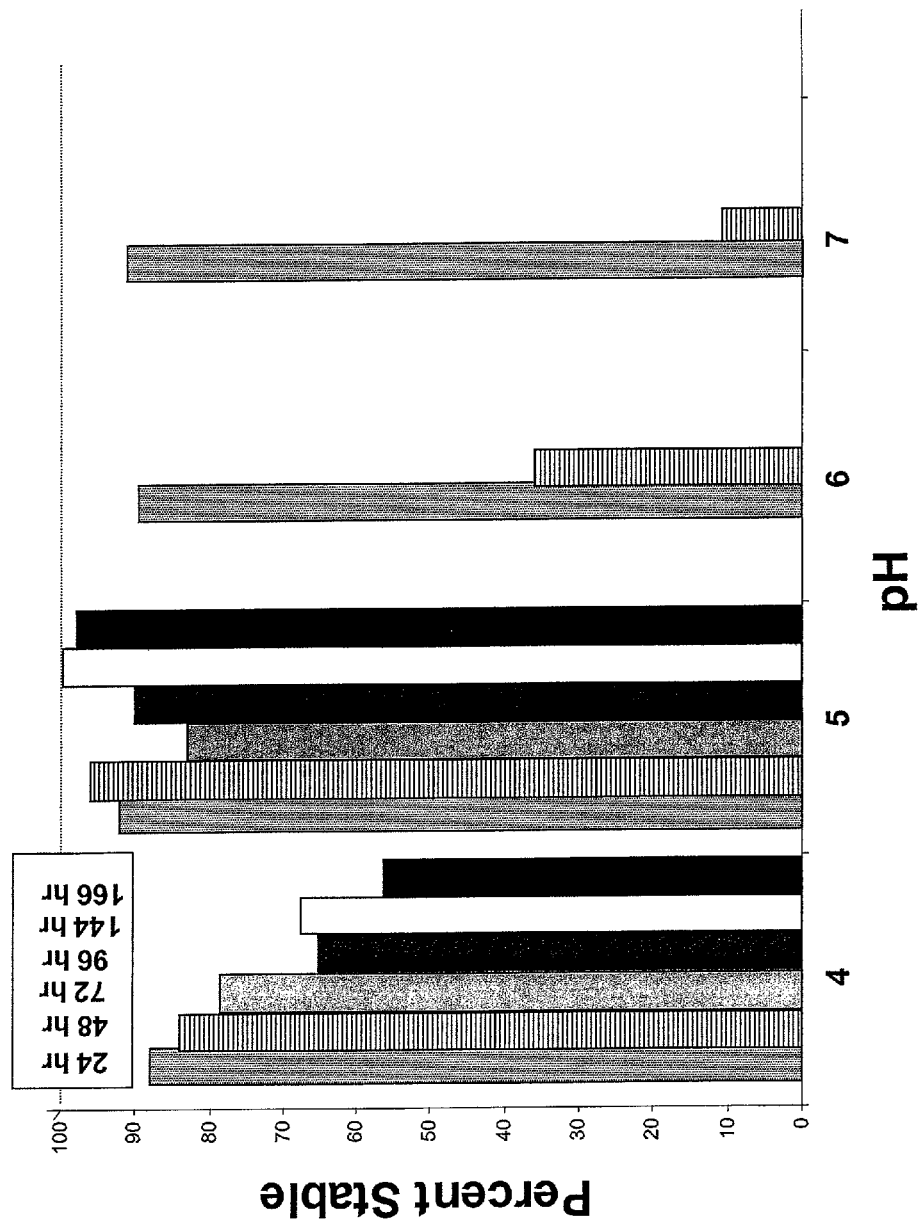
Fig. 1 Stability of Glucagon Cys$^{21}$-maleimidoPEG$_{5K}$ (37°C)

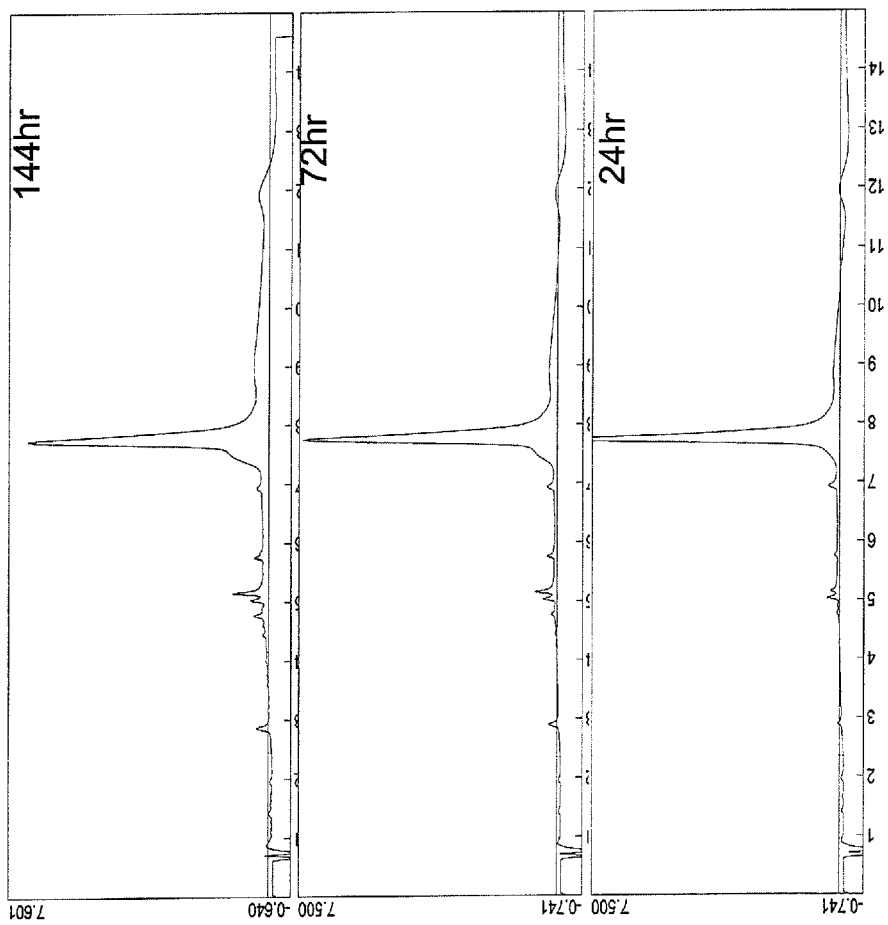
Fig. 2 HPLC Analysis of Glucagon Cys$^{21}$-maleimidoPEG$_{5K}$ at pH 5 (37°C)

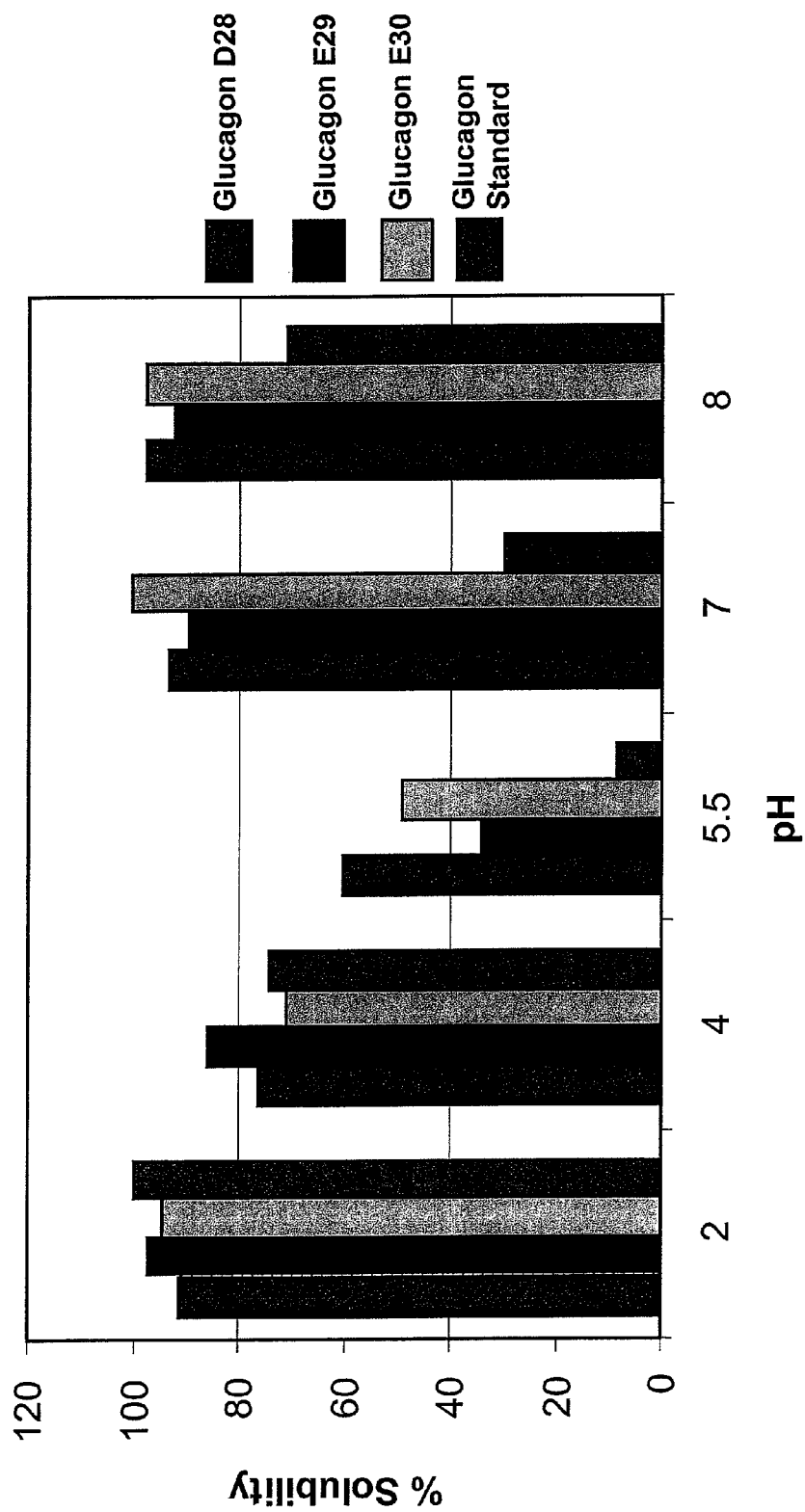
Fig. 3 Solubility and Stability of Glucagon Analogs after 60 hrs at 25°C at Various pHs

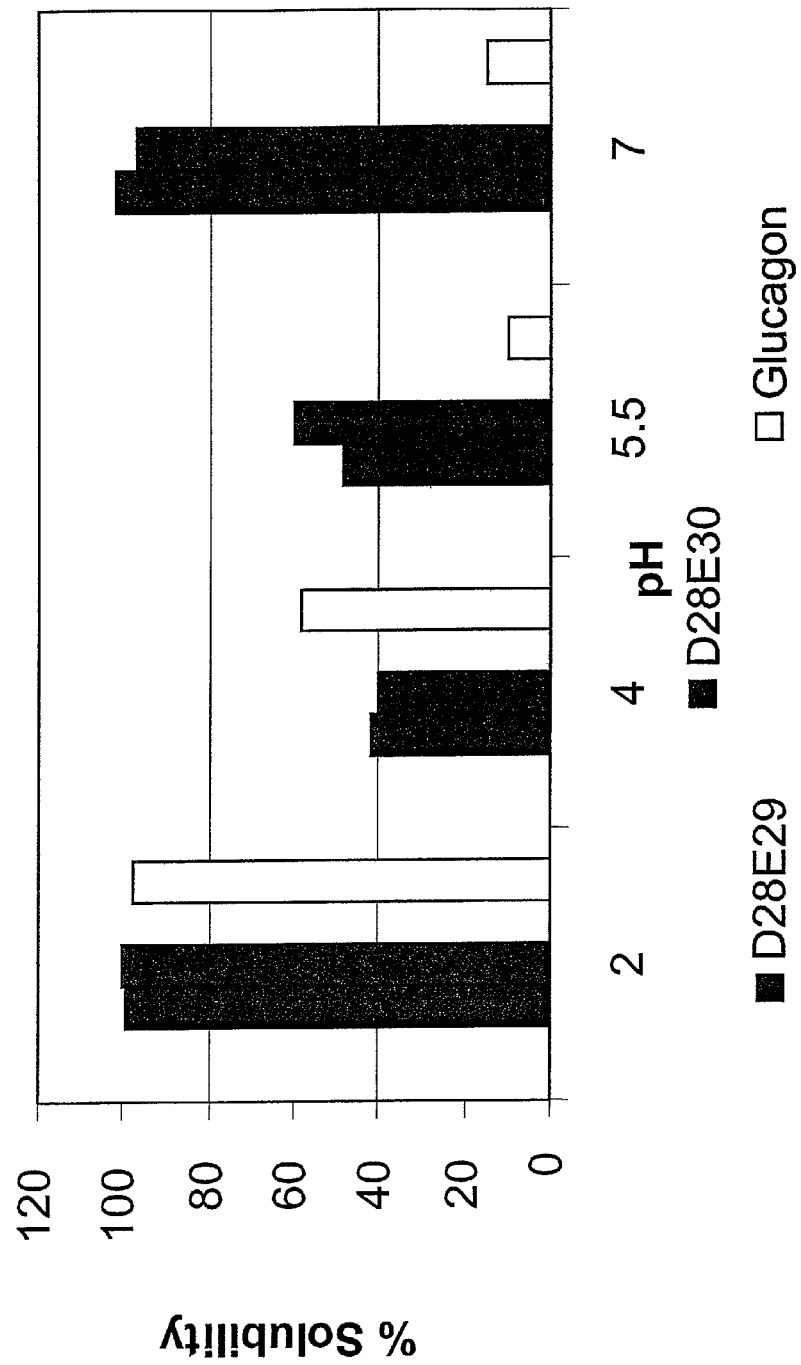
Fig. 4 Solubility of Anionic Glucagon Analogs
(24hrs at 25C and 24hrs at 4C)

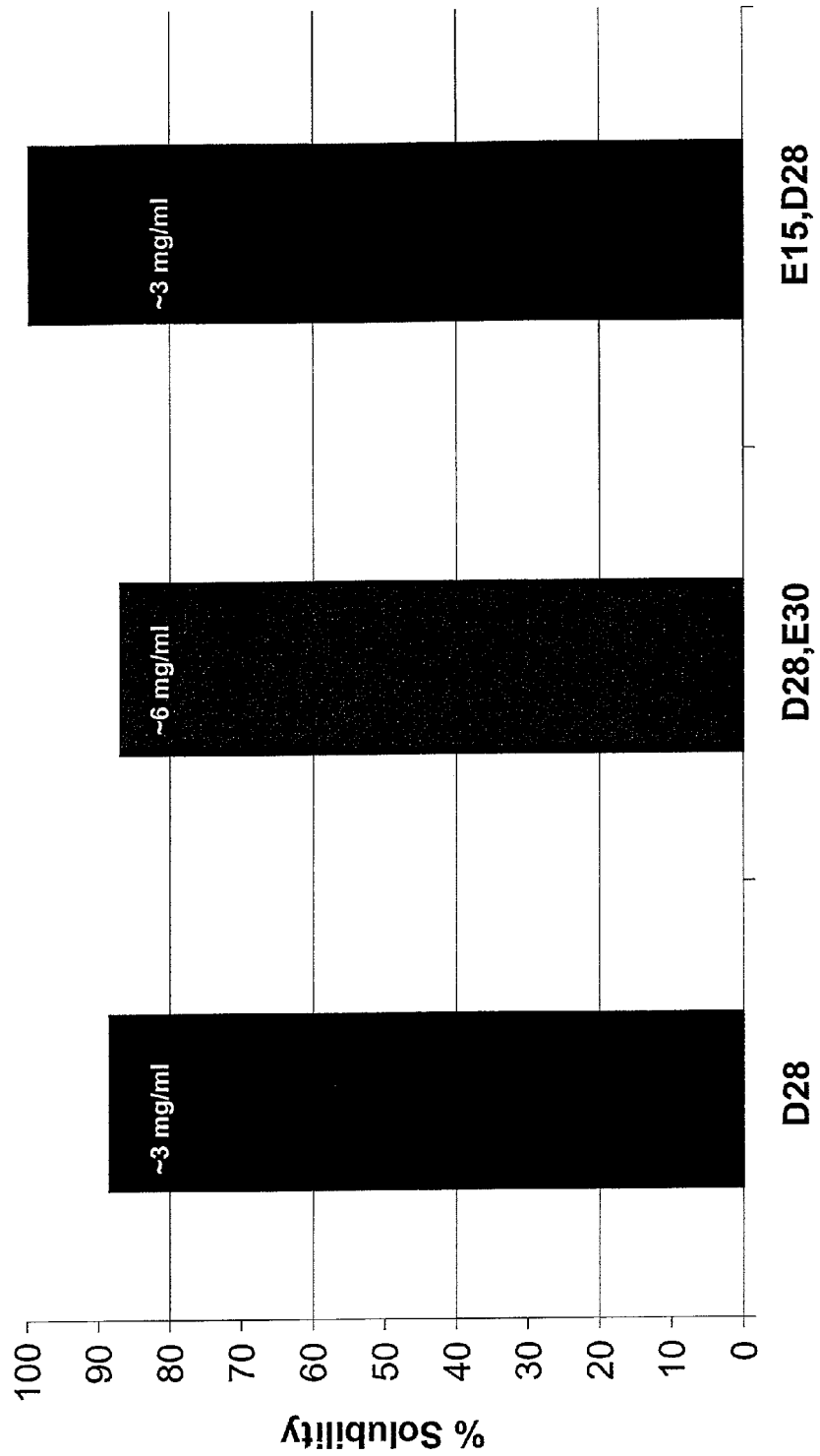

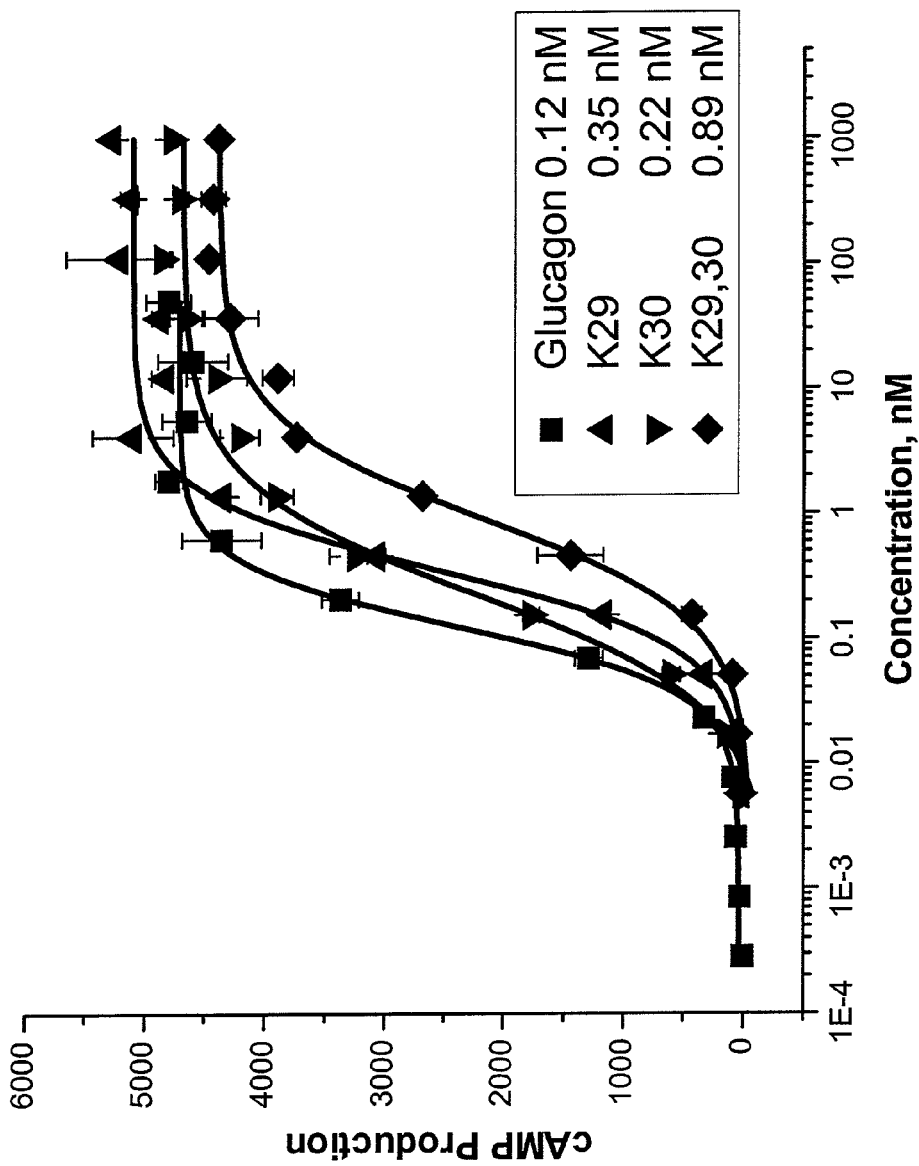

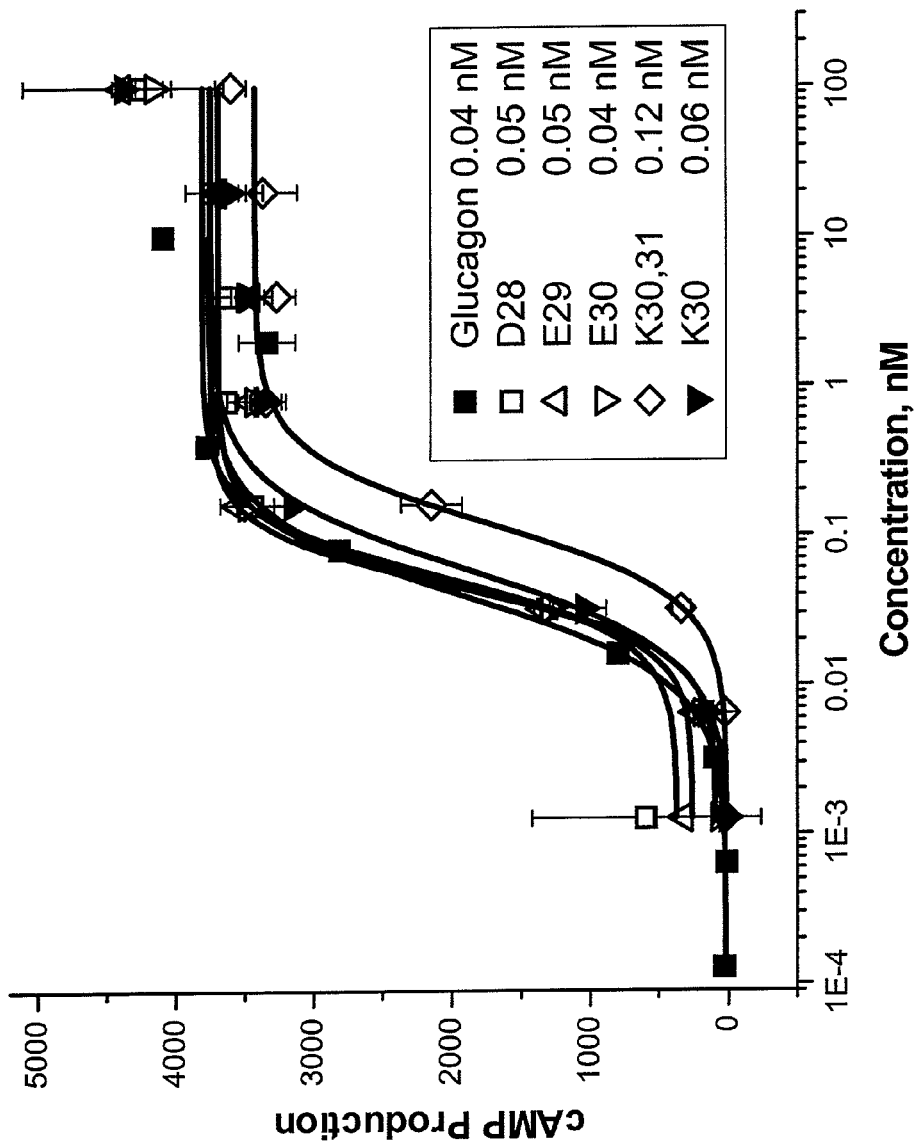

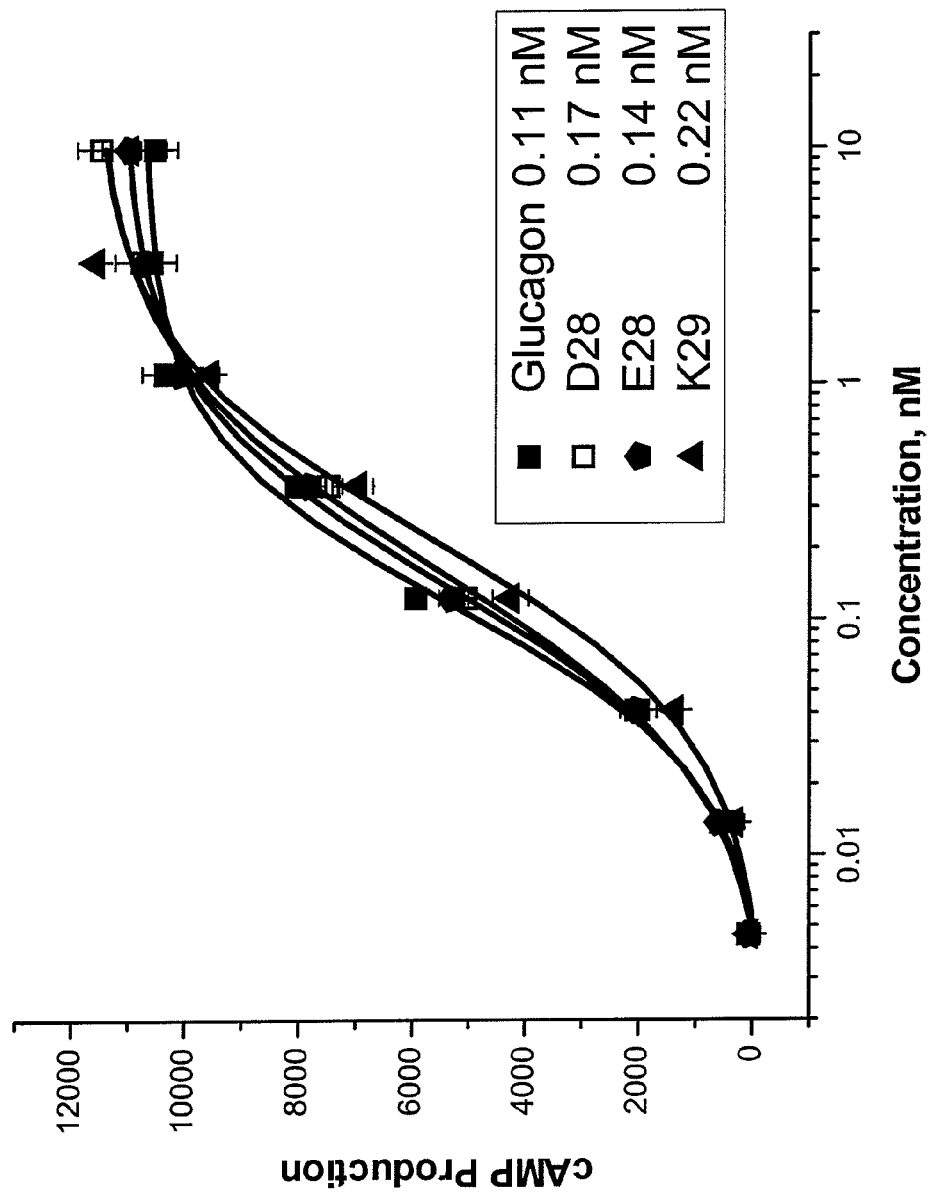
Fig. 8 Glucagon Receptor-mediated cAMP Induction

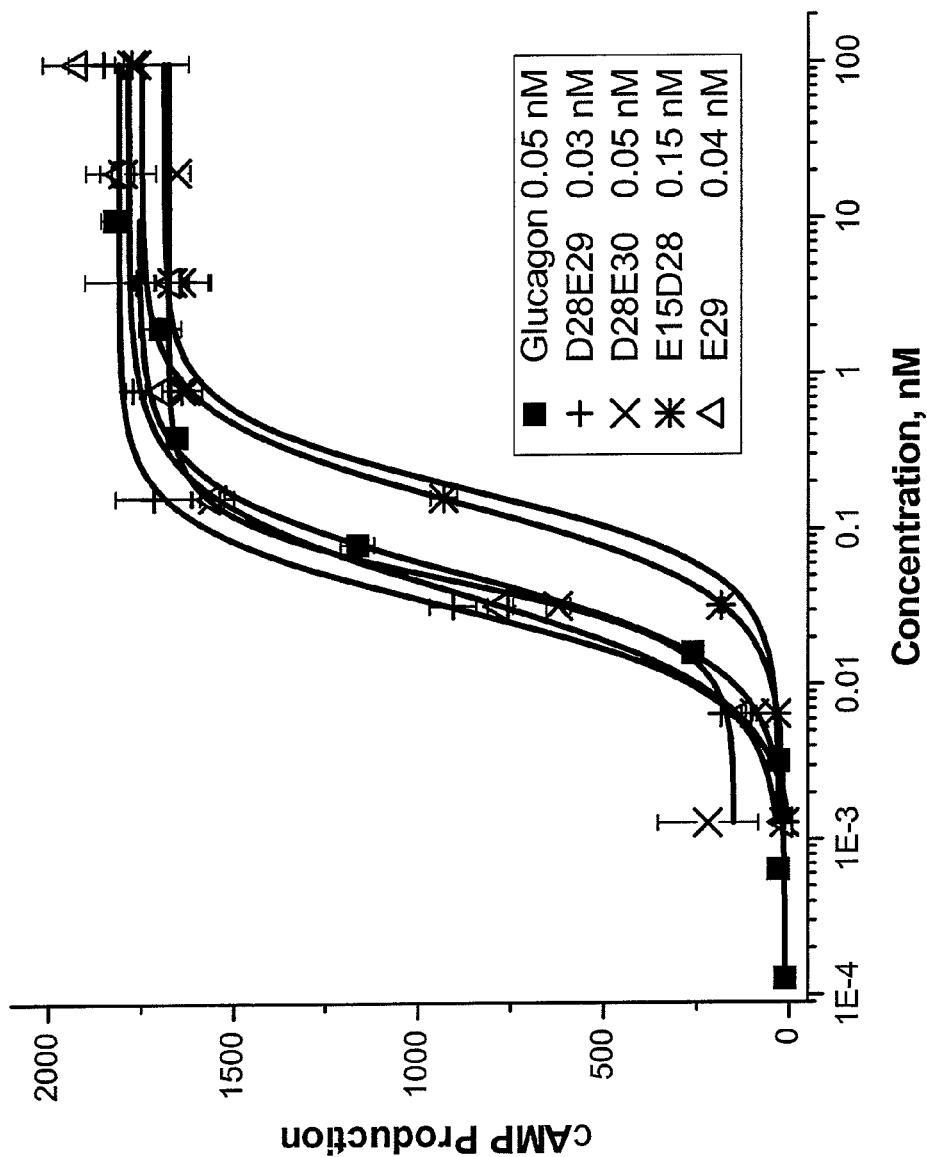

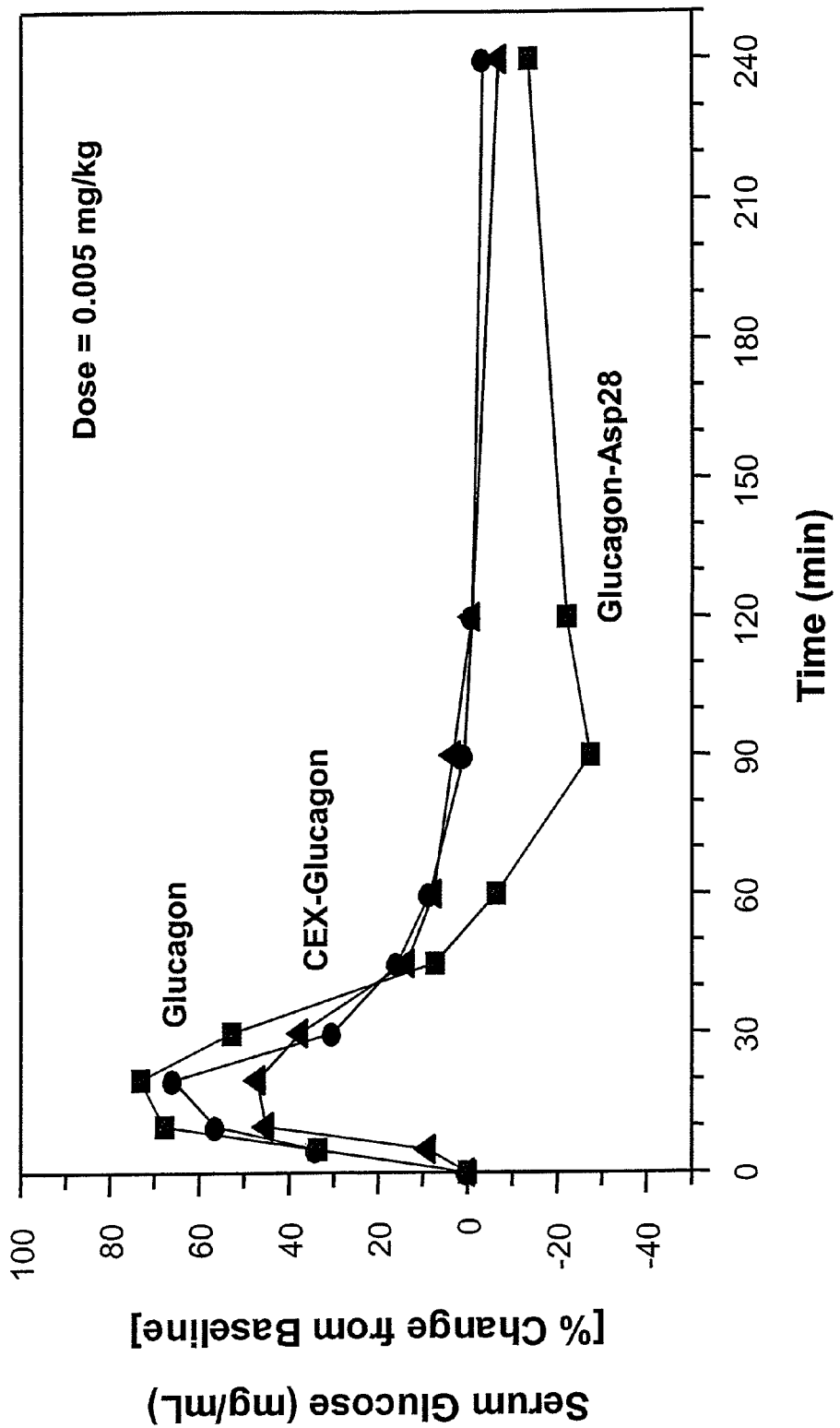

SEQUENCE LISTING

<160> NUMBER OF SEQ ID NOS: 38

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (16)..(16)
<223> OTHER INFORMATION: Xaa is Ser, Cys, Orn, homocysteine or acetyl
      phenylalanine
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 2

His Ser Gln Gly Thr Phe Thr Ser Asp Tyr Ser Lys Tyr Leu Asp Xaa
1               5                   10                  15

Arg Arg Ala Gln Asp Phe Val Gln Trp Leu Xaa Asp Thr
            20                  25

<210> SEQ ID NO 3
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (17)..(17)
<223> OTHER INFORMATION: Xaa is Arg, Cys, Orn, homocysteine or acetyl
      phenylalanine
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 3

His Ser Gln Gly Thr Phe Thr Ser Asp Tyr Ser Lys Tyr Leu Asp Ser
1               5                   10                  15

Xaa Arg Ala Gln Asp Phe Val Gln Trp Leu Xaa Asp Thr
            20                  25

<210> SEQ ID NO 4
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (21)..(21)
<223> OTHER INFORMATION: Xaa is Asp, Cys, Orn, homocysteine or acetyl
      phenylalanine

```
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 4

His Ser Gln Gly Thr Phe Thr Ser Asp Tyr Ser Lys Tyr Leu Asp Ser
1               5                   10                  15

Arg Arg Ala Gln Xaa Phe Val Gln Trp Leu Xaa Asp Thr
            20                  25

<210> SEQ ID NO 5
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (24)..(24)
<223> OTHER INFORMATION: Xaa is Gln, Cys, Orn, homocysteine or acetyl
      phenylalanine
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 5

His Ser Gln Gly Thr Phe Thr Ser Asp Tyr Ser Lys Tyr Leu Asp Ser
1               5                   10                  15

Arg Arg Ala Gln Asp Phe Val Xaa Trp Leu Xaa Asp Thr
            20                  25

<210> SEQ ID NO 6
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (21)..(21)
<223> OTHER INFORMATION: Xaa is Asp, Cys, Orn, homocysteine or acetyl
      phenylalanine
<220> FEATURE:
<221> NAME/KEY: MISC_FEATURE
<222> LOCATION: (24)..(24)
<223> OTHER INFORMATION: Xaa is Gln, Cys, Orn, homocysteine or acetyl
      phenylalanine
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 6

His Ser Gln Gly Thr Phe Thr Ser Asp Tyr Ser Lys Tyr Leu Asp Ser
1               5                   10                  15

Arg Arg Ala Gln Xaa Phe Val Xaa Trp Leu Xaa Asp Thr
            20                  25

<210> SEQ ID NO 7
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
<223> OTHER INFORMATION: Xaa is Met, Leu or Nle
<220> FEATURE:
```

```
<221> NAME/KEY: MISC_FEATURE
<222> LOCATION: (28)..(28)
<223> OTHER INFORMATION: Xaa is Lys, Arg, His, Asp, Glu, cysteic acid or
      homocysteic acid
<220> FEATURE:
<221> NAME/KEY: MISC_FEATURE
<222> LOCATION: (29)..(29)
<223> OTHER INFORMATION: Xaa is Thr, Lys, Arg, His, Asp, Glu, cysteic
      acid or homocysteic acid

<400> SEQUENCE: 7

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Xaa Xaa Xaa
            20                  25

<210> SEQ ID NO 8
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
<223> OTHER INFORMATION: Xaa is Met, Leu or Nle
<220> FEATURE:
<221> NAME/KEY: MISC_FEATURE
<222> LOCATION: (28)..(28)
<223> OTHER INFORMATION: Xaa is Asp or Glu
<220> FEATURE:
<221> NAME/KEY: MISC_FEATURE
<222> LOCATION: (29)..(29)
<223> OTHER INFORMATION: Xaa is Thr, Asp or Glu

<400> SEQUENCE: 8

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Xaa Xaa Xaa
            20                  25

<210> SEQ ID NO 9
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
<223> OTHER INFORMATION: Xaa is Met, Leu or Nle
<220> FEATURE:
<221> NAME/KEY: MISC_FEATURE
<222> LOCATION: (29)..(29)
<223> OTHER INFORMATION: Xaa is Asp or Glu

<400> SEQUENCE: 9

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Xaa Asn Xaa
            20                  25

<210> SEQ ID NO 10
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (27)..(27)
```

<223> OTHER INFORMATION: Xaa is Met, Leu or Nle

<400> SEQUENCE: 10

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Xaa Asp Thr
            20                  25

<210> SEQ ID NO 11
<211> LENGTH: 29
<212> TYPE: PRT
<213> ORGANISM: Artificial Sequence
<220> FEATURE:
<223> OTHER INFORMATION: Glucagon analogue

<400> SEQUENCE: 11

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asp Thr
            20                  25

<210> SEQ ID NO 12
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (29)..(29)
<223> OTHER INFORMATION: Xaa is Lys, Arg or His

<400> SEQUENCE: 12

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Xaa
            20                  25

<210> SEQ ID NO 13
<211> LENGTH: 29
<212> TYPE: PRT
<213> ORGANISM: Artificial Sequence
<220> FEATURE:
<223> OTHER INFORMATION: Glucagon analogue

<400> SEQUENCE: 13

His Ser Gln Gly Thr Phe Thr Ser Asp Tyr Ser Lys Tyr Leu Glu Ser
1               5                   10                  15

Arg Arg Ala Gln Asp Phe Val Gln Trp Leu Met Asp Thr
            20                  25

<210> SEQ ID NO 14
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (16)..(16)
<223> OTHER INFORMATION: pegylation
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 14

His Ser Gln Gly Thr Phe Thr Ser Asp Tyr Ser Lys Tyr Leu Asp Cys
1               5                   10                  15

Arg Arg Ala Gln Asp Phe Val Gln Trp Leu Xaa Asp Thr
            20                  25

<210> SEQ ID NO 15
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (17)..(17)
<223> OTHER INFORMATION: pegylation
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 15

His Ser Gln Gly Thr Phe Thr Ser Asp Tyr Ser Lys Tyr Leu Asp Ser
1               5                   10                  15

Cys Arg Ala Gln Asp Phe Val Gln Trp Leu Xaa Asp Thr
            20                  25

<210> SEQ ID NO 16
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (21)..(21)
<223> OTHER INFORMATION: pegylation
<220> FEATURE:
<221> NAME/KEY: MISC_FEATURE
<222> LOCATION: (27)..(27)
<223> OTHER INFORMATION: Xaa at position 27 = Met, Leu or Nle

<400> SEQUENCE: 16

His Ser Gln Gly Thr Phe Thr Ser Asp Tyr Ser Lys Tyr Leu Asp Ser
1               5                   10                  15

Arg Arg Ala Gln Cys Phe Val Gln Trp Leu Xaa Asp Thr
            20                  25

<210> SEQ ID NO 17
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (24)..(24)
<223> OTHER INFORMATION: pegylation
<220> FEATURE:
<221> NAME/KEY: MISC_FEATURE
<222> LOCATION: (27)..(27)
<223> OTHER INFORMATION: Xaa at position 27 = Met, Leu or Nle

<400> SEQUENCE: 17

His Ser Gln Gly Thr Phe Thr Ser Asp Tyr Ser Lys Tyr Leu Asp Ser
1               5                   10                  15

Arg Arg Ala Gln Asp Phe Val Cys Trp Leu Xaa Asp Thr
            20                  25

<210> SEQ ID NO 18

```
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (21)..(21)
<223> OTHER INFORMATION: pegylation
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 18

His Ser Gln Gly Thr Phe Thr Ser Asp Tyr Ser Arg Tyr Leu Asp Ser
1               5                   10                  15

Arg Arg Ala Gln Lys Phe Val Gln Trp Leu Xaa Asp Thr
            20                  25

<210> SEQ ID NO 19
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (24)..(24)
<223> OTHER INFORMATION: pegylation
<220> FEATURE:
<221> NAME/KEY: MISC_FEATURE
<222> LOCATION: (27)..(27)
<223> OTHER INFORMATION: Xaa is Met, Leu or Nle

<400> SEQUENCE: 19

His Ser Gln Gly Thr Phe Thr Ser Asp Tyr Ser Arg Tyr Leu Asp Ser
1               5                   10                  15

Arg Arg Ala Gln Asp Phe Val Lys Trp Leu Xaa Asp Thr
            20                  25

<210> SEQ ID NO 20
<211> LENGTH: 10
<212> TYPE: PRT
<213> ORGANISM: Artificial Sequence
<220> FEATURE:
<223> OTHER INFORMATION: peptide fragment representing the carboxy
      terminal 10 amino acids of Exendin-4

<400> SEQUENCE: 20

Gly Pro Ser Ser Gly Ala Pro Pro Pro Ser
1               5                   10

<210> SEQ ID NO 21
<211> LENGTH: 8
<212> TYPE: PRT
<213> ORGANISM: Artificial Sequence
<220> FEATURE:
<223> OTHER INFORMATION: peptide fragment representing the carboxy
      terminal 8 amino acids of oxyntomodulin

<400> SEQUENCE: 21

Lys Arg Asn Arg Asn Asn Ile Ala
1               5

<210> SEQ ID NO 22
<211> LENGTH: 4
<212> TYPE: PRT
<213> ORGANISM: Artificial Sequence
<220> FEATURE:
```

<223> OTHER INFORMATION: peptide fragment representing the amino 4 amino
      acids of oxyntomodulin carboxy terminus of SEQ ID NO: 21

<400> SEQUENCE: 22

Lys Arg Asn Arg
1

<210> SEQ ID NO 23
<211> LENGTH: 10
<212> TYPE: PRT
<213> ORGANISM: Artificial Sequence
<220> FEATURE:
<223> OTHER INFORMATION: peptide fragment representing the carboxy
      terminal 10 amino acids of Exendin-4
<220> FEATURE:
<221> NAME/KEY: MOD_RES
<222> LOCATION: (10)..(10)
<223> OTHER INFORMATION: AMIDATION

<400> SEQUENCE: 23

Gly Pro Ser Ser Gly Ala Pro Pro Pro Ser
1               5                   10

<210> SEQ ID NO 24
<211> LENGTH: 39
<212> TYPE: PRT
<213> ORGANISM: Artificial Sequence
<220> FEATURE:
<223> OTHER INFORMATION: Glucagon analogue

<400> SEQUENCE: 24

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asp Thr Gly Pro Ser
            20                  25                  30

Ser Gly Ala Pro Pro Pro Ser
        35

<210> SEQ ID NO 25
<211> LENGTH: 37
<212> TYPE: PRT
<213> ORGANISM: Artificial Sequence
<220> FEATURE:
<223> OTHER INFORMATION: Glucagon analogue

<400> SEQUENCE: 25

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asp Thr Lys Arg Asn
            20                  25                  30

Arg Asn Asn Ile Ala
        35

<210> SEQ ID NO 26
<211> LENGTH: 33
<212> TYPE: PRT
<213> ORGANISM: Artificial Sequence
<220> FEATURE:
<223> OTHER INFORMATION: Glucagon analogue

<400> SEQUENCE: 26

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asp Thr Lys Arg Asn
            20                  25                  30

Arg

<210> SEQ ID NO 27
<211> LENGTH: 29
<212> TYPE: PRT
<213> ORGANISM: Artificial Sequence
<220> FEATURE:
<223> OTHER INFORMATION: Glucagon analogue

<400> SEQUENCE: 27

His Ser Gln Gly Thr Phe Thr Ser Asp Tyr Ser Lys Tyr Leu Asp Ser
1               5                   10                  15

Cys Arg Ala Gln Asp Phe Val Gln Trp Leu Met Asn Thr
            20                  25

<210> SEQ ID NO 28
<211> LENGTH: 39
<212> TYPE: PRT
<213> ORGANISM: Artificial Sequence
<220> FEATURE:
<223> OTHER INFORMATION: Glucagon Analogue

<400> SEQUENCE: 28

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Gly Pro Ser
            20                  25                  30

Ser Gly Ala Pro Pro Pro Ser
        35

<210> SEQ ID NO 29
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MOD_RES
<222> LOCATION: (24)..(24)
<223> OTHER INFORMATION: 2-butyrolactone bound through thiol group of
      cys

<400> SEQUENCE: 29

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 30
<211> LENGTH: 29
<212> TYPE: PRT
<213> ORGANISM: Artificial Sequence
<220> FEATURE:
<223> OTHER INFORMATION: Glucagon Analogue
<220> FEATURE:
<221> NAME/KEY: MOD_RES
<222> LOCATION: (24)..(24)
<223> OTHER INFORMATION: carboxymethyl group bound through thiol group
      of cys

<400> SEQUENCE: 30

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

```
<210> SEQ ID NO 31
<211> LENGTH: 39
<212> TYPE: PRT
<213> ORGANISM: Artificial Sequence
<220> FEATURE:
<223> OTHER INFORMATION: Glucagon analogue

<400> SEQUENCE: 31

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Gly Pro Ser
            20                  25                  30

Ser Gly Ala Pro Pro Pro Ser
        35

<210> SEQ ID NO 32
<211> LENGTH: 30
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (30)..(30)
<223> OTHER INFORMATION: Xaa is Asp, Glu, Lys, Arg or His

<400> SEQUENCE: 32

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asp Thr Xaa
            20                  25                  30

<210> SEQ ID NO 33
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
<222> LOCATION: (15)..(15)
<223> OTHER INFORMATION: Xaa is Asp, Glu, cysteic acid, homoglutamic
      acid or homocysteic acid
<220> FEATURE:
<221> NAME/KEY: MISC_FEATURE
<222> LOCATION: (27)..(27)
<223> OTHER INFORMATION: Xaa is Met, Leu or Nle
<220> FEATURE:
<221> NAME/KEY: MISC_FEATURE
<222> LOCATION: (28)..(28)
<223> OTHER INFORMATION: Xaa is Asn, Lys, Arg, His, Asp or Glu
<220> FEATURE:
<221> NAME/KEY: MISC_FEATURE
<222> LOCATION: (29)..(29)
<223> OTHER INFORMATION: Xaa is Thr, Lys, Arg, His, Asp or Glu

<400> SEQUENCE: 33

His Ser Gln Gly Thr Phe Thr Ser Asp Tyr Ser Lys Tyr Leu Xaa Ser
1               5                   10                  15

Arg Arg Ala Gln Asp Phe Val Gln Trp Leu Xaa Xaa Xaa
            20                  25

<210> SEQ ID NO 34
<211> LENGTH: 29
<212> TYPE: PRT
<213> ORGANISM: Artificial Sequence
<220> FEATURE:
<223> OTHER INFORMATION: Glucagon analogue
<220> FEATURE:
<221> NAME/KEY: MISC_FEATURE
```

```
<222> LOCATION: (15)..(15)
<223> OTHER INFORMATION: Xaa is Asp, Glu, cysteic acid, homoglutamic
      acid or homocysteic acid
<220> FEATURE:
<221> NAME/KEY: MISC_FEATURE
<222> LOCATION: (27)..(27)
<223> OTHER INFORMATION: Xaa is Met, Leu or Nle
<220> FEATURE:
<221> NAME/KEY: MISC_FEATURE
<222> LOCATION: (28)..(28)
<223> OTHER INFORMATION: Xaa is Asn or an acidic amino acid
<220> FEATURE:
<221> NAME/KEY: MISC_FEATURE
<222> LOCATION: (29)..(29)
<223> OTHER INFORMATION: Xaa is Thr or an acidic amino acid

<400> SEQUENCE: 34

His Ser Gln Gly Thr Phe Thr Ser Asp Tyr Ser Lys Tyr Leu Xaa Ser
1               5                   10                  15

Arg Arg Ala Gln Asp Phe Val Gln Trp Leu Xaa Xaa Xaa
            20                  25

<210> SEQ ID NO 35
<211> LENGTH: 39
<212> TYPE: PRT
<213> ORGANISM: Artificial Sequence
<220> FEATURE:
<223> OTHER INFORMATION: Glucagon analogue

<400> SEQUENCE: 35

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Glu Thr Gly Pro Ser
            20                  25                  30

Ser Gly Ala Pro Pro Pro Ser
            35

<210> SEQ ID NO 36
<211> LENGTH: 37
<212> TYPE: PRT
<213> ORGANISM: Artificial Sequence
<220> FEATURE:
<223> OTHER INFORMATION: Glucagon analogue

<400> SEQUENCE: 36

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Glu Thr Lys Arg Asn
            20                  25                  30

Arg Asn Asn Ile Ala
        35

<210> SEQ ID NO 37
<211> LENGTH: 33
<212> TYPE: PRT
<213> ORGANISM: Artificial Sequence
<220> FEATURE:
<223> OTHER INFORMATION: Glucagon analogue

<400> SEQUENCE: 37

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Glu Thr Lys Arg Asn
            20                  25                  30

Arg
```

```
<210> SEQ ID NO 38
<211> LENGTH: 29
<212> TYPE: PRT
<213> ORGANISM: Artificial Sequence
<220> FEATURE:
<223> OTHER INFORMATION: Glucagon analogue

<400> SEQUENCE: 38

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Glu Thr
            20                  25
```

GLUCAGON ANALOGS EXHIBITING ENHANCED SOLUBILITY IN PHYSIOLOGICAL PH BUFFERS

CROSS REFERENCE TO RELATED APPLICATIONS

This application is a U.S. national counterpart application of international application serial No. PCT/US2008/050099 filed Jan. 3, 2008, which claims priority to U.S. Provisional Patent Application No. 60/878,919, filed Jan. 5, 2007. The entire disclosures of PCT/US2008/050099 and U.S. Ser. No. 60/878,919 are hereby incorporated by reference.

BACKGROUND

Hypoglycemia occurs when blood glucose levels drops too low to provide enough energy for the body's activities. In adults or children older than 10 years, hypoglycemia is uncommon except as a side effect of diabetes treatment, but it can result from other medications or diseases, hormone or enzyme deficiencies, or tumors. When blood glucose begins to fall, glucagon, a hormone produced by the pancreas, signals the liver to break down glycogen and release glucose, causing blood glucose levels to rise toward a normal level. However for diabetics, this glucagon response to hypoglycemia may be impaired, making it harder for glucose levels to return to the normal range.

Hypoglycemia is a life threatening event that requires immediate medical attention. The administration of glucagon is an established medication for treating acute hypoglycemia and it can restore normal levels of glucose within minutes of administration. When glucagon is used in the acute medical treatment of hypoglycemia, a crystalline form of glucagon is solubilized with a dilute acid buffer and the solution is injected intramuscularly. While this treatment is effective, the methodology is cumbersome and dangerous for someone that is semi-conscious. Accordingly, there is a need for a glucagon analog that maintains the biological performance of the parent molecule but is sufficiently soluble and stable, under relevant physiological conditions, that it can be pre-formulated as a solution, ready for injection.

Additionally, diabetics are encouraged to maintain near normal blood glucose levels to delay or prevent microvascular complications. Achievement of this goal usually requires intensive insulin therapy. In striving to achieve this goal, physicians have encountered a substantial increase in the frequency and severity of hypoglycemia in their diabetic patients. Accordingly, improved pharmaceuticals and methodologies are needed for treating diabetes that are less likely to induce hypoglycemia than current insulin therapies.

As described herein, high potency glucagon agonists are provided that exhibit enhanced biophysical stability and aqueous solubility at physiological pH in pharmaceutical compositions suitable for commercial use. Native glucagon is neither soluble, nor stable in the physiological pH range and thus must be manufactured as a dry product that requires reconstitution and immediate use. The glucagon analogs described herein have enhanced physical properties that render them superior for use in current medicinal settings where the native hormone is currently employed. These compounds can be used in accordance with one embodiment to prepare pre-formulated solutions ready for injection to treat hypoglycemia. Alternatively, the glucagon agonists can be co-administered with insulin to buffer the effects of insulin to allow for a more stable maintenance of blood glucose levels. In addition, other beneficial uses of compositions comprising the modified glucagon peptides disclosed herein are described in detail below.

SUMMARY

One embodiment of the invention provides glucagon peptides that retain glucagon receptor activity and exhibit improved solubility relative to the native glucagon peptide (SEQ ID NO: 1). Native glucagon exhibits poor solubility in aqueous solution, particularly at physiological pH, with a tendency to aggregate and precipitate over time. In contrast, the glucagon peptides of one embodiment of the invention exhibit at least 2-fold, 5-fold, or even higher solubility compared to native glucagon at a pH between 6 and 8, for example, at pH 7 after 24 hours at 25° C.

In one embodiment the glucagon peptides retain at least 10%, 20%, 30%, 40%, 50%, 60%, 70%, 75% activity, 80% activity, 85% activity, or 90% of the activity of native glucagon. In one embodiment, the glucagon peptides of the present invention have potency greater than glucagon. Any of the glucagon peptides of the invention may additionally exhibit improved stability and/or reduced degradation, for example, retaining at least 95% of the original peptide after 24 hours at 25° C.

In accordance with one embodiment a glucagon peptide is provided wherein the peptide is modified by amino acid substitutions and/or additions that introduce a charged amino acid into the C-terminal portion of the peptide, and in one embodiment at a position C-terminal to position 27 of SEQ ID NO: 1. Optionally, one, two or three charged amino acids may be introduced within the C-terminal portion, and in one embodiment C-terminal to position 27. In accordance with one embodiment the native amino acid(s) at positions 28 and/or 29 are substituted with a charged amino acid, and/or one to three charged amino acids are added to the C-terminus of the peptide. In exemplary embodiments, one, two or all of the charged amino acids are negatively charged. Additional modifications, e.g. conservative substitutions, may be made to the glucagon peptide that still allow it to retain glucagon activity.

In accordance with one exemplary embodiment the glucagon peptide comprises an amino acid sequence of SEQ ID NO: 11, or an analog thereof that contains 1 to 3 further amino acid modifications relative to native glucagon, or a glucagon agonist analog thereof. SEQ ID NO: 11 represents a modified glucagon peptide wherein the asparagine residue at position 28 of the native protein has been substituted with an aspartic acid. In another exemplary embodiment the glucagon peptide comprises an amino acid sequence of SEQ ID NO: 38, wherein the asparagine residue at position 28 of the native protein has been substituted with glutamic acid. Other exemplary embodiments include glucagon peptides of SEQ ID NOS: 24, 25, 26, 33, 35, 36 and 37.

The solubility of any of the foregoing compounds can be further improved by attaching a hydrophilic moiety to the peptide. In one embodiment the hydrophilic moiety is a polyethylene glycol chain or other water soluble polymer that is covalently linked to the side chain of an amino acid residue at position 16, 17, 21 or 24 of said glucagon peptide. The polyethylene glycol chain in accordance with one embodiment has a molecular weight selected from the range of about 500 to about 40,000 Daltons. The present invention further encompasses pharmaceutically acceptable salts of said glucagon agonists.

In other exemplary embodiments, any of the foregoing compounds can be further modified to alter its pharmaceutical properties by the addition of a second peptide to the carboxy terminus of the glucagon peptide. In one embodiment a glucagon peptide is covalently bound through a peptide bond to a second peptide, wherein the second peptide comprises a sequence selected from the group consisting of SEQ ID NO: 20, SEQ ID NO: 21 and SEQ ID NO: 22.

In yet further exemplary embodiments, any of the foregoing compounds can be further modified to improve stability by modifying the amino acid at position 15 of SEQ ID NO: 1 to reduce degradation of the peptide over time, especially in acidic or alkaline buffers.

In accordance with one embodiment a pharmaceutical composition is provided comprising any of the novel glucagon peptides disclosed herein, preferably at a purity level of at least 90%, 91%, 92%, 93%, 94%, 95%, 96%, 97%, 98% or 99%, and a pharmaceutically acceptable diluent, carrier or excipient. Such compositions may contain a glucagon peptide at a concentration of at least 0.5 mg/ml, 1 mg/ml, 2 mg/ml, 3 mg/ml, 4 mg/ml, 5 mg/ml, or higher. In one embodiment the pharmaceutical compositions comprise aqueous solutions that are sterilized and optionally stored within various containers. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

In accordance with one embodiment a method of rapidly increasing glucose level or treating hypoglycemia using a pre-formulated aqueous composition is provided. The method comprises the step of administering an effective amount of an aqueous solution comprising a novel modified glucagon peptide of the present disclosure. In another embodiment a method is provided for inducing the temporary paralysis of the intestinal tract. The method comprises the step of administering one or more of the glucagon peptides disclosed herein to a patient in need thereof.

In yet another embodiment a method of reducing weight gain or inducing weight loss is provided, which involves administering an effective amount of an aqueous solution comprising a glucagon peptide of the invention. In further embodiments, methods of treating diabetes involving co-administering insulin and a glucagon peptide of the invention are provided.

Exemplary glucagon peptides are selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NO: 33, wherein amino acid 29 of the glucagon peptide is bound to a second peptide through a peptide bond, and said second peptide comprises the sequence of SEQ ID NO: 20, SEQ ID NO: 21 or SEQ ID NO: 22. In one embodiment the glucagon peptide is pegylated. In one embodiment the method comprises the step of administering a peptide comprising the sequence of SEQ ID NO: 24, SEQ ID NO: 25, and SEQ ID NO: 26, wherein a polyethylene chain is covalently linked to amino acid position 21 or at position 24.

BRIEF DESCRIPTION OF THE DRAWINGS

FIG. 1 is a bar graph representing the stability of Glucagon $Cys^{21}$maleimidoPEG$_{5K}$ at 37° C. incubated for 24, 48, 72, 96, 144 and 166 hours, respectively.

FIG. 2 represents data generated from HPLC analysis of Glucagon $Cys^{21}$maleimidoPEG$_{5K}$ at pH 5 incubated at 37° C. for 24, 72 or 144 hours, respectively.

FIG. 3 represents data showing the solubility of glucagon analogs (D28, E29, E30) relative to native glucagon after 60 hours at 25° C. at pH of 2, 4, 5.5, 7 and 8, respectively.

FIG. 4 represents data showing the solubility of glucagon analogs (E15D28, D28E29 and D28E30) relative to native glucagon after 24 hours at 25° C. and then 24 hours a 4° C. at pH of 2, 4, 5.5 and 7, respectively.

FIG. 5 represents the maximum solubility of glucagon analogs D28, D28E30 and E15, D28 after 24 hours, pH 7 at 4° C.

FIG. 6 represents data showing a glucagon receptor mediated cAMP induction by glucagon analogs (K29 ▲, K30 ▼, and K29K30 ♦) relative to native glucagon ■.

FIG. 7 represents data showing a glucagon receptor mediated cAMP induction by glucagon analogs (D28 □, E29 Δ, E30 ∇, K30K31 ◊ and K30, ▼) relative to native glucagon ■.

FIG. 8 represents data showing a glucagon receptor mediated cAMP induction by glucagon analogs (D28 □, E28 ♠ and K29, ▲) relative to native glucagon ■.

FIG. 9 represents data showing a glucagon receptor mediated cAMP induction by glucagon analogs (D28E29+, D28E30 X, E15D28* and E29 Δ) relative to native glucagon ■.

FIG. 10 represents data showing the change in serum glucose concentrations in beagle dogs after intramuscular administration of glucagon and glucagon analogs. The animals were administered a 0.005 mg/kg dose of either glucagon, a glucagon analog comprising glucagon with the sequence of SEQ ID NO: 31 linked to the carboxy terminus of glucagon (glucagon-CEX) or a glucagon analog comprising an aspartic acid substitution at amino acid 28 (glucagon-Asp28) SEQ ID NO: 11.

DETAILED DESCRIPTION

Definitions

In describing and claiming the invention, the following terminology will be used in accordance with the definitions set forth below.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, the term "treating" includes prophylaxis of the specific disorder or condition, or alleviation of the symptoms associated with a specific disorder or condition and/or preventing or eliminating said symptoms.

As used herein an "effective" amount or a "therapeutically effective amount" of a glucagon peptide refers to a nontoxic but sufficient amount of the peptide to provide the desired effect. For example one desired effect would be the prevention or treatment of hypoglycemia, as measured, for example, by an increase in blood glucose level. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as subcutaneous, intramuscular, intraspinal, or intravenous.

As used herein, the term "purified" and like terms relate to the isolation of a molecule or compound in a faun that is substantially free of contaminants normally associated with the molecule or compound in a native or natural environment. As used herein, the term "purified" does not require absolute purity; rather, it is intended as a relative definition. The term "purified polypeptide" is used herein to describe a polypeptide which has been separated from other compounds including, but not limited to nucleic acid molecules, lipids and carbohydrates.

The term "isolated" requires that the referenced material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated.

A "glucagon peptide" as used herein includes any peptide comprising, either the amino acid sequence of SEQ ID NO: 1, or any analog of the amino acid sequence of SEQ ID NO: 1, including amino acid substitutions, additions, or deletions, or post translational modifications (e.g. methylation, acylation, ubiquitination and the like) of the peptide, that stimulates glucagon or GLP-1 receptor activity, as measured by cAMP production using the assay described in Example 13.

The term "glucagon agonist" refers to a complex comprising a glucagon peptide that stimulates glucagon receptor activity, as measured by cAMP production using the assay described in Example 13.

As used herein a "glucagon agonist analog" is a glucagon peptide comprising a sequence selected from the group consisting of SEQ ID NO: 7, SEQ ID NO: 8, SEQ ID NO: 9, SEQ ID NO: 10, SEQ ID NO: 11, SEQ ID NO: 12 and SEQ ID NO: 13 or a analog of such a sequence that has been modified to include one or more conservative amino acid substitutions at positions 2, 5, 7, 10, 11, 12, 13, 14, 16, 17, 18, 19, 20, 21, 24, 27, 28 or 29.

As used herein an amino acid "modification" refers to a substitution, addition or deletion of an amino acid, and includes substitution with or addition of any of the 20 amino acids commonly found in human proteins, as well as atypical or non-naturally occurring amino acids. Throughout the application, all references to a particular amino acid position by number (e.g. position 28) refer to the amino acid at that position in native glucagon (SEQ ID NO:1) or the corresponding amino acid position in any analogs thereof. For example, a reference herein to "position 28" would mean the corresponding position 27 for a glucagon analog in which the first amino acid of SEQ ID NO: 1 has been deleted. Similarly, a reference herein to "position 28" would mean the corresponding position 29 for a glucagon analog in which one amino acid has been added before the N-terminus of SEQ ID NO: 1.

As used herein an amino acid "substitution" refers to the replacement of one amino acid residue by a different amino acid residue.

As used herein, the term "conservative amino acid substitution" is defined herein as exchanges within one of the following five groups:

I. Small aliphatic, nonpolar or slightly polar residues:
   Ala, Ser, Thr, Pro, Gly;
II. Polar, negatively charged residues and their amides:
   Asp, Asn, Glu, Gln, cysteic acid and homocysteic acid;
III. Polar, positively charged residues:
   His, Arg, Lys; Ornithine (Orn)
IV. Large, aliphatic, nonpolar residues:
   Met, Leu, Ile, Val, Cys, Norleucine (Nle), homocysteine
V. Large, aromatic residues:
   Phe, Tyr, Trp, acetyl phenylalanine As used herein the general term "polyethylene glycol" or "PEG", refers to mixtures of condensation polymers of ethylene oxide and water, in a branched or straight chain, represented by the general formula $H(OCH_2CH_2)_nOH$, wherein n is at least 9. Absent any further characterization, the term is intended to include polymers of ethylene glycol with an average total molecular weight selected from the range of 500 to 40,000 Daltons. "polyethylene glycol" or "PEG" is used in combination with a numeric suffix to indicate the approximate average molecular weight thereof. For example, PEG-5,000 refers to polyethylene glycol having a total molecular weight average of about 5,000.

As used herein the term "pegylated" and like terms refers to a compound that has been modified from its native state by linking a polyethylene glycol polymer to the compound. A "pegylated glucagon peptide" is a glucagon peptide that has a PEG chain covalently bound to the glucagon peptide.

As used herein a general reference to a peptide is intended to encompass peptides that have modified amino and carboxy termini. For example, an amino acid chain comprising an amide group in place of the terminal carboxylic acid is intended to be encompassed by an amino acid sequence designating the standard amino acids.

As used herein a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein a "dimer" is a complex comprising two subunits covalently bound to one another via a linker. The term dimer, when used absent any qualifying language, encompasses both homodimers and heterodimers. A homodimer comprises two identical subunits, whereas a heterodimer comprises two subunits that differ, although the two subunits are substantially similar to one another.

As used herein the term "pH stabilized glucagon peptide" refers to a glucagon agonist analog that exhibits superior stability and solubility, relative to native glucagon, in aqueous buffers in the broadest pH range used for pharmacological purposes.

As used herein the term "charged amino acid" refers to an amino acid that comprises a side chain that is negatively charged (i.e., de-protonated) or positively charged (i.e., protonated) in aqueous solution at physiological pH. For example negatively charged amino acids include aspartic acid, glutamic acid, cysteic acid, homocysteic acid, and homoglutamic acid, whereas positively charged amino acids include arginine, lysine and histidine. Charged amino acids include the charged amino acids among the 20 amino acids commonly found in human proteins, as well as atypical or non-naturally occurring amino acids.

As used herein the term "acidic amino acid" refers to an amino acid that comprises a second acidic moiety, including for example, a carboxylic acid or sulfonic acid group.

Embodiments

Applicants have discovered that native glucagon can be modified by introducing charge at its carboxy terminus to enhance the solubility of the peptide while retaining the agonist properties of the peptide. The enhanced solubility allows for the preparation and storage of glucagon solutions at near neutral pH. Formulating glucagon solutions at relatively neutral pHs (e.g. pH of about 6.0 to about 8.0) improves the long term stability of the glucagon peptides. Accordingly, one embodiment of the present invention is directed to a glucagon agonist that has been modified relative to the wild type peptide of His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr (SEQ ID NO: 1) to improve the peptide's solubility in aqueous solutions, particularly at a pH ranging from about 5.5 to about 8.0, while retaining the native peptide's biological activity. In one embodiment charge is added to the peptide by the substitution of native non-charged amino acids with charged amino acids selected from the group consisting of lysine, arginine, histidine, aspartic acid and glutamic acid, or by the addition of charged amino acids to the amino or carboxy terminus of the peptide. Surprisingly, applicants have discovered that substituting the normally occurring amino acid at position 28 and/or 29 with charged amino acids, and/or the addition of one to two charged amino acids at the carboxy terminus of the glucagon peptide, enhances the solubility and stability of the glucagon peptides in aqueous solutions at physiologically relevant pHs (i.e., a pH of about 6.5 to about 7.5) by at least 5-fold and by as much as 30-fold.

Accordingly, glucagon peptides of one embodiment of the invention retain glucagon activity and exhibit at least 2-fold, 5-fold, 10-fold, 15-fold, 25-fold, 30-fold or greater solubility relative to native glucagon at a given pH between about 5.5 and 8, e.g., pH 7, when measured after 24 hours at 25° C. Any of the glucagon peptides disclosed herein may additionally exhibit improved stability at a pH within the range of 5.5 to 8, for example, retaining at least 75%, 80%, 90%, 95%, 96%, 97%, 98% or 99% of the original peptide after 24 hours at 25° C. The glucagon peptides may include additional modifications that alter its pharmaceutical properties, e.g. increased potency, prolonged half-life in circulation, increased shelf-life, reduced precipitation or aggregation, and/or reduced degradation, e.g., reduced occurrence of cleavage or chemical modification after storage.

In one embodiment a glucagon peptide with improved solubility may be prepared, for example, by introducing one, two, three or more charged amino acid(s) to the C-terminal portion of native glucagon, and in one embodiment at a position C-terminal to position 27. Such a charged amino acid can be introduced, for example by substituting a native amino acid with a charged amino acid, e.g. at positions 28 or 29, or alternatively by adding a charged amino acid, e.g. after position 27, 28 or 29. In exemplary embodiments, one, two, three or all of the charged amino acids are negatively charged. In other embodiments, one, two, three or all of the charged amino acids are positively charged. In specific exemplary embodiments, the glucagon peptide may comprise any one or two of the following modifications: substitution of N28 with E; substitution of N28 with D; substitution of T29 with D; substitution of T29 with E; insertion of E after position 27, 28 or 29; insertion of D after position 27, 28 or 29. For example, E28E30, D28E30

Additional modifications may be made to the glucagon peptide which may further increase solubility and/or stability and/or glucagon activity. The glucagon peptide may alternatively comprise other modifications that do not substantially affect solubility or stability, and that do not substantially decrease glucagon activity. In exemplary embodiments, the glucagon peptide may comprise a total of 1, up to 2, up to 3, up to 4, up to 5, up to 6, up to 7, up to 8, up to 9, or up to 10 amino acid modifications relative to the native glucagon sequence.

Exemplary modifications include but are not limited to:

conservative substitutions, for example, conservative substitutions at one or more of positions 2, 5, 7, 10, 11, 12, 13, 14, 16, 17, 18, 19, 20, 21, 24, 27, 28 or 29;

modification of the aspartic acid at position 15, for example, by substitution with glutamic acid, homoglutamic acid, cysteic acid or homocysteic acid, which may reduce degradation;

addition of a hydrophilic moiety such as the water soluble polymer polyethylene glycol, as described herein, e.g. at position 16, 17, 20, 21, 24 or 29, which may increase solubility and/or half-life;

modification of the amino acid at position 27, for example, by substitution with methionine, leucine or norleucine;

modifications at position 1 or 2 as described herein;

C-terminal extensions as described herein;

homodimerization or heterodimerization as described herein; and combinations of the above.

In accordance with one embodiment the native glucagon peptide of SEQ ID NO: 1 is modified by the substitution of the native amino acid at position 28 and/or 29 with a negatively charged amino acid (e.g., aspartic acid or glutamic acid) and optionally the addition of a negatively charged amino acid (e.g., aspartic acid or glutamic acid) to the carboxy terminus of the peptide. In an alternative embodiment the native glucagon peptide of SEQ ID NO: 1 is modified by the substitution of the native amino acid at position 29 with a positively charged amino acid (e.g., lysine, arginine or histidine) and optionally the addition of one or two positively charged amino acid (e.g., lysine, arginine or histidine) on the carboxy terminus of the peptide. In accordance with one embodiment a glucagon analog having improved solubility and stability is provided wherein the analog comprises the amino acid sequence of SEQ ID NO: 34 with the proviso that at least one amino acids at position, 28, or 29 is substituted with an acidic amino acid and/or an additional acidic amino acid is added at the carboxy terminus of SEQ ID NO: 34. In one embodiment the acidic amino acids are independently selected from the group consisting of Asp, Glu, cysteic acid and homocysteic acid.

In accordance with one embodiment a glucagon agonist having improved solubility and stability is provided wherein the agonist comprises the amino acid sequence of SEQ ID NO: 33, wherein at least one of the amino acids at positions 27, 28 or 29 is substituted with a non-native amino acid residue (i.e. at least one amino acid present at position 27, 28 or 29 of the analog is an acid amino acid different from the amino acid present at the corresponding position in SEQ ID NO: 1). In accordance with one embodiment a glucagon agonist is provided comprising the sequence of SEQ ID NO: 33 with the proviso that when the amino acid at position 28 is asparagine and the amino acid at position 29 is threonine, the peptide further comprises one to two amino acids, independently selected from the group consisting of Lys, Arg, His, Asp or Glu, added to the carboxy terminus of the glucagon peptide.

It has been reported that certain positions of the native glucagon peptide can be modified while retaining at least some of the activity of the parent peptide. Accordingly, applicants anticipate that one or more of the amino acids located at positions at positions 2, 5, 7, 10, 11, 12, 13, 14, 16, 17, 18, 19, 20, 21, 24, 27 or 29 of the peptide of SEQ ID NO: 11 can be substituted with an amino acid different from that present in the native glucagon peptide, and still retain the enhanced potency, physiological pH stability and biological activity of the parent glucagon peptide. For example, in accordance with one embodiment the methionine residue present at position 27 of the native peptide is changed to leucine or norleucine to prevent oxidative degradation of the peptide.

In one embodiment a glucagon analog of SEQ ID NO: 33 is provided wherein 1 to 6 amino acids, selected from positions 1, 2, 5, 7, 10, 11, 12, 13, 14, 16, 17, 18, 19, 20, 21 or 24 of the analog differ from the corresponding amino acid of SEQ ID NO: 1. In accordance with another embodiment a glucagon analog of SEQ ID NO: 33 is provided wherein 1 to 3 amino acids selected from positions 1, 2, 5, 7, 10, 11, 12, 13, 14, 16, 17, 18, 19, 20, 21 or 24 of the analog differ from the corresponding amino acid of SEQ ID NO: 1. In another embodiment, a glucagon analog of SEQ ID NO: 7, SEQ ID NO: 8 or SEQ ID NO: 34 is provided wherein 1 to 2 amino acids selected from positions 1, 2, 5, 7, 10, 11, 12, 13, 14, 16, 17, 18, 19, 20, 21 or 24 of the analog differ from the corresponding amino acid of SEQ ID NO: 1, and in a further embodiment those one to two differing amino acids represent conservative amino acid substitutions relative to the amino acid present in the native sequence (SEQ ID NO: 1). In one embodiment a glucagon peptide of SEQ ID NO: 11 or SEQ ID NO: 13 is provided wherein the glucagon peptide further comprises one, two or three amino acid substitutions at positions selected from positions 2, 5, 7, 10, 11, 12, 13, 14, 16, 17, 18, 19, 20, 21, 24, 27 or 29. In one embodiment the substitutions at positions 2, 5, 7, 10, 11, 12, 13, 14, 16, 17, 18, 19, 20, 27 or 29 are conservative amino acid substitutions.

In one embodiment a glucagon agonist is provided comprising an analog peptide of SEQ ID NO: 1 wherein the analog differs from SEQ ID NO: 1 by having an amino acid other than serine at position 2 and by having an acidic amino acid substituted for the native amino acid at position 28 or 29 or an acidic amino acid added to the carboxy terminus of the peptide of SEQ ID NO: 1. In one embodiment the acidic amino acid is aspartic acid or glutamic acid. In one embodiment a glucagon analog of SEQ ID NO: 9, SEQ ID NO: 12, SEQ ID NO: 13 or SEQ ID NO: 32 is provided wherein the analog differs from the parent molecule by a substitution at position 2. More particularly, position 2 of the analog peptide is substituted with an amino acid selected from the group consisting of d-serine, alanine, glycine, n-methyl serine and amino isobutyric acid.

In another embodiment a glucagon agonist is provided comprising an analog peptide of SEQ ID NO: 1 wherein the analog differs from SEQ ID NO: 1 by having an amino acid other than histidine at position 1 and by having an acidic amino acid substituted for the native amino acid at position 28 or 29 or an acidic amino acid added to the carboxy terminus of the peptide of SEQ ID NO: 1. In one embodiment the acidic amino acid is aspartic acid or glutamic acid. In one embodiment a glucagon analog of SEQ ID NO: 9, SEQ ID NO: 12, SEQ ID NO: 13 or SEQ ID NO: 32 is provided wherein the analog differs from the parent molecule by a substitution at position 1. More particularly, position 1 of the analog peptide is substituted with an amino acid selected from the group consisting of d-histidine, desaminohistidine, hydroxyl-histidine, acetyl-histidine and homo-histidine.

In accordance with one embodiment the modified glucagon peptide comprises a sequence selected from the group consisting of SEQ ID NO: 9, SEQ ID NO: 12, SEQ ID NO: 13 and SEQ ID NO: 32. In a further embodiment a glucagon peptide is provided comprising a sequence of SEQ ID NO: 9, SEQ ID NO: 12, SEQ ID NO: 13 or SEQ ID NO: 32 further comprising one to two amino acids, added to the c-terminus of SEQ ID NO: 9, SEQ ID NO: 12, SEQ ID NO: 13 or SEQ ID NO: 32, wherein the additional amino acids are independently selected from the group consisting of Lys, Arg, His, Asp Glu, cysteic acid or homocysteic acid. In one embodiment the additional amino acids added to the carboxy terminus are selected from the group consisting of Lys, Arg, His, Asp or Glu or in a further embodiment the additional amino acids are Asp or Glu.

In another embodiment the glucagon peptide comprises the sequence of SEQ ID NO: 7 or a glucagon agonist analog thereof. In one embodiment the peptide comprising a sequence selected from the group consisting of SEQ ID NO: 8, SEQ ID NO: 10, SEQ ID NO: 11, SEQ ID NO: 12 and SEQ ID NO: 13. In another embodiment the peptide comprising a sequence selected from the group consisting of SEQ ID NO: 8, SEQ ID NO: 10 and SEQ ID NO: 11. In one embodiment the glucagon peptide comprises the sequence of SEQ ID NO: 8, SEQ ID NO: 10 and SEQ ID NO: 11 further comprising an additional amino acid, selected from the group consisting of Asp and Glu, added to the c-terminus of the glucagon peptide. In one embodiment the glucagon peptide comprises the sequence of SEQ ID NO: 11 or SEQ ID NO: 13, and in a further embodiment the glucagon peptide comprises the sequence of SEQ ID NO: 11.

In accordance with one embodiment a glucagon agonist is provided comprising a modified glucagon peptide selected from the group consisting of:

$NH_2$-His-Ser-Gln-Gly-Thr-Phe-Thr-Ser-Asp-Tyr-Ser-Lys-Tyr-Leu-Xaa-Ser-Arg-Arg-Ala-Gln-Asp-Phe-Val-Gln-Trp-Leu-Xaa-Xaa-Xaa-R (SEQ ID NO: 34), $NH_2$-His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asp-Thr-R (SEQ ID NO: 11) and $NH_2$-His-Ser-Gln-Gly-Thr-Phe-Thr-Ser-Asp-Tyr-Ser-Xaa-Tyr-Leu-Glu-Ser-Arg-Arg-Ala-Gln-Asp-Phe-Val-Gln-Trp-Leu-Met-Asp-Thr-R (SEQ ID NO: 13)

wherein Xaa at position 15 is Asp, Glu, cysteic acid, homoglutamic acid or homocysteic acid, the Xaa at position 28 is Asn or an acidic amino acid and the Xaa at position 29 is Thr or an acidic amino acid and R is an acidic amino acid, COOH or $CONH_2$, with the proviso that an acidic acid residue is present at one of positions 28, 29 or 30. In one embodiment R is COOH, and in another embodiment R is $CONH_2$.

The present disclosure also encompasses glucagon fusion peptides wherein a second peptide has been fused to the c-terminus of the glucagon peptide to enhance the stability and solubility of the glucagon peptide. More particularly, the fusion glucagon peptide may comprise a glucagon agonist analog comprising a glucagon peptide NH$_2$-His-Ser-Gln-Gly-Thr-Phe-Thr-Ser-Asp-Tyr-Ser-Lys-Tyr-Leu-Xaa-Ser-Arg-Arg-Ala-Gln-Asp-Phe-Val-Gln-Trp-Leu-Xaa-Xaa-Xaa-R (SEQ ID NO: 34), wherein R is an acidic amino acid or a bond and an amino acid sequence of SEQ ID NO: 20 (GPSSGAPPPS), SEQ ID NO: 21 (KRNRNNIA) or SEQ ID NO: 22 (KRNR) linked to the carboxy terminal amino acid of the glucagon peptide. In one embodiment the glucagon peptide is selected from the group consisting of SEQ ID NO: 33, SEQ ID NO: 7 or SEQ ID NO: 8 further comprising an amino acid sequence of SEQ ID NO: 20 (GPSSGAPPPS), SEQ ID NO: 21 (KRNRNNIA) or SEQ ID NO: 22 (KRNR) linked to the carboxy terminal amino acid of the glucagon peptide. In one embodiment the glucagon fusion peptide comprises SEQ ID NO: 2, SEQ ID NO: 3, SEQ ID NO: 4, SEQ ID NO: 5 and SEQ ID NO: 6 or a glucagon agonist analog thereof, further comprising an amino acid sequence of SEQ ID NO: 20 (GPSSGAPPPS), SEQ ID NO: 21 (KRNRNNIA) or SEQ ID NO: 22 (KRNR) linked to amino acid 29 of the glucagon peptide. In accordance with one embodiment the fusion peptide further comprises a PEG chain linked to an amino acid at position 16, 17, 21 or 24, wherein the PEG chain is selected from the range of 500 to 40,000 Daltons. In one embodiment the amino acid sequence of SEQ ID NO: 20 (GPSSGAPPPS), SEQ ID NO: 21 (KRNRNNIA) or SEQ ID NO: 22 (KRNR) is bound to amino acid 29 of the glucagon peptide through a peptide bond. In one embodiment the glucagon peptide portion of the glucagon fusion peptide comprises a sequence selected from the group consisting of SEQ ID NO: 10, SEQ ID NO: 11 and SEQ ID NO: 13. In one embodiment the glucagon peptide portion of the glucagon fusion peptide comprises the sequence of SEQ ID NO: 11 or SEQ ID NO: 13, wherein a PEG chain is linked at position 21 or 24, respectively.

In another embodiment the glucagon peptide sequence of the fusion peptide comprises the sequence of SEQ ID NO: 11, further comprising an amino acid sequence of SEQ ID NO: 20 (GPSSGAPPPS), SEQ ID NO: 21 (KRNRNNIA) or SEQ ID NO: 22 (KRNR) linked to amino acid 29 of the glucagon peptide. In one embodiment the glucagon fusion peptide comprises a sequence selected from the group consisting of SEQ ID NO: 24, SEQ ID NO: 25 and SEQ ID NO: 26. Typically the fusion peptides of the present invention will have a c-terminal amino acid with the standard carboxylic acid group. However, analogs of those sequences wherein the C-terminal amino acid has an amide substituted for the carboxylic acid are also encompassed as embodiments. In accordance with one embodiment the fusion glucagon peptide comprises a glucagon agonist analog selected from the group consisting of SEQ ID NO: 10, SEQ ID NO: 11 and SEQ ID NO: 13, further comprising an amino acid sequence of SEQ ID NO: 23 (GPSSGAPPPS-CONH$_2$) linked to amino acid 29 of the glucagon peptide.

The glucagon agonists of the present invention can be further modified to improve the peptide's solubility and stability in aqueous solutions while retaining the biological activity of the glucagon peptide. In accordance with one embodiment, introduction of hydrophilic groups at one or more positions selected from positions 16, 17, 20, 21, 24 and 29 of the peptide of SEQ ID NO: 11, or a glucagon agonist analog thereof, are anticipated to improve the solubility and stability of the pH stabilize glucagon analog. More particularly, in one embodiment the glucagon peptide of SEQ ID NO: 10, SEQ ID NO: 11, SEQ ID NO: 13, or SEQ ID NO: 32 is modified to comprise one or more hydrophilic groups covalently linked to the side chains of amino acids present at positions 21 and 24 of the glucagon peptide.

In accordance with one embodiment, the glucagon peptide of SEQ ID NO: 11 is modified to contain one or more amino acid substitution at positions 16, 17, 20, 21, 24 and/or 29, wherein the native amino acid is substituted with an amino acid having a side chain suitable for crosslinking with hydrophilic moieties, including for example, PEG. The native peptide can be substituted with a naturally occurring amino acid or a synthetic (non-naturally occurring) amino acid. Synthetic or non-naturally occurring amino acids refer to amino acids that do not naturally occur in vivo but which, nevertheless, can be incorporated into the peptide structures described herein.

In one embodiment, a glucagon agonist of SEQ ID NO: 10, SEQ ID NO: 11 or SEQ ID NO: 13 is provided wherein the native glucagon peptide sequence has been modified to contain a naturally occurring or synthetic amino acid in at least one of positions 16, 17, 21 and 24 of the native sequence, wherein the amino acid substitute further comprises a hydrophilic moiety. In one embodiment the substitution is at position 21 or 24, and in a further embodiment the hydrophilic moiety is a PEG chain. In one embodiment the glucagon peptide of SEQ ID NO: 11 is substituted with at least one cysteine residue, wherein the side chain of the cysteine residue is further modified with a thiol reactive reagent, including for example, maleimido, vinyl sulfone, 2-pyridylthio, haloalkyl, and haloacyl. These thiol reactive reagents may contain carboxy, keto, hydroxyl, and ether groups as well as other hydrophilic moieties such as polyethylene glycol units. In an alternative embodiment, the native glucagon peptide is substituted with lysine, and the side chain of the substituting lysine residue is further modified using amine reactive reagents such as active esters (succinimido, anhydride, etc) of carboxylic acids or aldehydes of hydrophilic moieties such as polyethylene glycol. IN one embodiment the glucagon peptide is selected fowl the group consisting of SEQ ID NO: 14, SEQ ID NO: 15, SEQ ID NO: 16, SEQ ID NO: 17, SEQ ID NO: 18 and SEQ ID NO: 19.

In accordance with one embodiment the pegylated glucagon peptide comprises two or more polyethylene chains covalently bound to the glucagon peptide wherein the total molecular weight of the glucagon chains is about 1,000 to about 5,000 Daltons. In one embodiment the pegylated glucagon agonist comprises a peptide of SEQ ID NO: 6, wherein a PEG chain is covalently linked to the amino acid residue at position 21 and at position 24, and wherein the combined molecular weight of the two PEG chains is about 1,000 to about 5,000 Daltons. In another embodiment the pegylated glucagon agonist comprises a peptide of SEQ ID NO: 6, wherein a PEG chain is covalently linked to the amino acid residue at position 21 and at position 24, and wherein the combined molecular weight of the two PEG chains is about 5,000 to about 20,000 Daltons.

The polyethylene glycol chain may be in the form of a straight chain or it may be branched. In accordance with one embodiment the polyethylene glycol chain has an average molecular weight selected from the range of about 500 to about 40,000 Daltons. In one embodiment the polyethylene glycol chain has a molecular weight selected from the range of about 500 to about 5,000 Daltons. In another embodiment the polyethylene glycol chain has a molecular weight of about 20,000 to about 40,000 Daltons.

As described in detail in the Examples, the glucagon agonists of the present invention have enhanced biophysical stability and aqueous solubility in solutions of physiological pH, while retaining or demonstrating enhanced bioactivity relative to the native peptide. Accordingly, the glucagon agonists of the present invention are believed to be suitable for any use that has previously been described for the native glucagon peptide. Therefore, the modified glucagon peptides described herein can be used to treat hypoglycemia, to increase blood glucose level, to induce temporary paralysis of the gut for radiological uses, to reduce and maintain body weight, as adjunctive therapy with insulin, or to treat other metabolic diseases that result from low blood levels of glucagon.

One aspect of the present disclosure is directed to a pre-formulated aqueous solution of the presently disclosed glucagon agonist for use in treating hypoglycemia. The improved stability and/or solubility of the agonist compositions described herein allow for the preparation of pre-formulated aqueous solutions of glucagon for rapid administration and treatment of hypoglycemia. Accordingly, in one embodiment a solution comprising a glucagon agonist of the present invention is provided for administration to a patient suffering from hypoglycemia. In one embodiment a solution comprising a pegylated glucagon agonist as disclosed herein is provided for administration to a patient suffering from hypoglycemia, wherein the total molecular weight of the PEG chains linked to the pegylated glucagon agonist is between about 500 to about 5,000 Daltons. In one embodiment the pegylated glucagon agonist comprises a peptide selected from the group consisting of SEQ ID NO: 14, SEQ ID NO: 15, SEQ ID NO: 16, SEQ ID NO: 17, SEQ ID NO: 18 and SEQ ID NO: 19, and glucagon agonist analogs of thereof, wherein the side chain of an amino acid residue at position 16, 17, 21 or 24 of said glucagon peptide is covalently bound to the polyethylene glycol chain. In one embodiment, the pegylated glucagon agonist comprises the peptide of SEQ ID NO: 16, wherein the amino acid residue at position 21 of the peptide is covalently linked to polyethylene glycol. In one embodiment, the pegylated glucagon agonist comprises the peptide of SEQ ID NO: 17, wherein the amino acid residue at position 24 of the peptide is covalently linked to polyethylene glycol.

The method of treating hypoglycemia in accordance with the present invention comprises the steps of administering the presently disclosed glucagon agonists to a patient using any standard route of administration, including parenterally, such as intravenously, intraperitoneally, subcutaneously or intramuscularly, intrathecally, transdermally, rectally, orally, nasally or by inhalation. In one embodiment the composition is administered subcutaneously or intramuscularly. In one embodiment, the composition is administered parenterally and the glucagon composition is prepackaged in a syringe. Advantageously, the aqueous stable glucagon analogs disclosed herein exhibit superior stability and solubility in aqueous buffers in the broadest pH range used for pharmacological purposes, relative to native glucagon. The use of the stabilized glucagon analogs disclosed herein allow for the preparation and storage of glucagon agonist solutions at physiological pH for long periods of time.

Applicants have discovered that pegylated glucagon peptides can be prepared that retain the parent peptide's bioactivity and specificity. However, increasing the length of the PEG chain, or attaching multiple PEG chains to the peptide, such that the total molecular weight of the linked PEG is greater than 5,000 Daltons, begins to delay the time action of the modified glucagon. In accordance with one embodiment, a glucagon peptide of SEQ ID NO: 11 or SEQ ID NO: 13, or a glucagon agonist analog thereof, is provided wherein the peptide comprises one or more polyethylene glycol chains, wherein the total molecular weight of the linked PEG is greater than 5,000 Daltons, and in one embodiment is greater than 10,000 Daltons, but less than 40,000 Daltons. Such modified glucagon peptides have a delayed time of activity but without loss of the bioactivity. Accordingly, such compounds can be administered prophylactically to extend the effect of the administered glucagon peptide.

Glucagon peptides that have been modified to be covalently bound to a PEG chain having a molecular weight of greater than 10,000 Daltons can be administered in conjunction with insulin to buffer the actions of insulin and help to maintain stable blood glucose levels in diabetics. The modified glucagon peptides of the present disclosure can be co-administered with insulin as a single composition, simultaneously administered as separate solutions, or alternatively, the insulin and the modified glucagon peptide can be administered at different time relative to one another. In one embodiment the composition comprising insulin and the composition comprising the modified glucagon peptide are administered within 12 hours of one another. The exact ratio of the modified glucagon peptide relative to the administered insulin will be dependent in part on determining the glucagon levels of the patient, and can be determined through routine experimentation.

In accordance with one embodiment a composition is provided comprising insulin and a modified glucagon peptide selected from the group consisting of SEQ ID NO: 2, SEQ ID NO: 3, SEQ ID NO: 4, SEQ ID NO: 5 and glucagon agonist analogs thereof, wherein the modified glucagon peptide further comprises a polyethylene glycol chain covalently bound to an amino acid side chain at position 16, 17, 21 or 24. In one embodiment the composition is an aqueous solution comprising insulin and the glucagon analog. In embodiments wherein the glucagon peptide comprises the sequence of SEQ ID NO: 11 or SEQ ID NO: 13, the peptide may further comprise a polyethylene glycol chain covalently bound to an amino acid side chain at position 16, 17, 21 or 24. In one embodiment the molecular weight of the PEG chain of the modified glucagon peptide is greater than 10,000 Daltons. In one embodiment the pegylated glucagon peptide comprises a peptide selected from the group consisting of SEQ ID NO: 11 and SEQ ID NO: 13 wherein the side chain of an amino acid residue at position 21 or 24 of said glucagon peptide is covalently bound to the polyethylene glycol chain. In one embodiment the polyethylene glycol chain has a molecular weight of about 10,000 to about 40,000.

In accordance with one embodiment the modified glucagon peptides disclosed herein are used to induce temporary paralysis of the intestinal tract. This method has utility for radiological purposes and comprises the step of administering an effective amount of a pharmaceutical composition comprising a pegylated glucagon peptide, a glucagon peptide comprising a c-terminal extension or a dimer of such peptides. In one embodiment the glucagon peptide comprises a sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13. In one embodiment the glucagon peptide further comprises a PEG chain, of about 1,000 to 40,000 Daltons is covalently bound to an amino acid residue at position 21 or 24. In one embodiment the glucagon peptide is selected from the group consisting of SEQ ID NO: 14, SEQ ID NO: 15, SEQ ID NO: 16 and SEQ ID NO: 17. In one embodiment the PEG chain has a molecular weight of about 500 to about 5,000 Daltons.

In a further embodiment the composition used to induce temporary paralysis of the intestinal tract comprises a first modified glucagon peptide and a second modified glucagon peptide, wherein the first modified peptide comprises a sequence selected from the group consisting of SEQ ID NO: 10, SEQ ID NO: 11 and SEQ ID NO: 13, optionally linked to a PEG chain of about 500 to about 5,000 Daltons, and the second peptide comprises a covalently linked PEG chain of about 10,000 to about 40,000 Daltons. In this embodiment the PEG chain of each peptide is covalently bound to an amino acid residue at either position 21 or 24 of the respective peptide, and independent of one another.

Oxyntomodulin, a naturally occurring digestive hormone found in the small intestine, has been reported to cause weight loss when administered to rats or humans (see Diabetes 2005; 54:2390-2395). Oxyntomodulin is a 37 amino acid peptide that contains the 29 amino acid sequence of glucagon (i.e. SEQ ID NO: 1) followed by an 8 amino acid carboxy terminal extension of SEQ ID NO: 23 (KRNRNNIA). Accordingly, applicants believe that the bioactivity of oxyntomodulin can be retained (i.e. appetite suppression and induced weight loss/weight maintenance), while improving the solubility and stability of the compound and improving the pharmacokinetics, by substituting the glucagon peptide portion of oxyntomodulin with the modified glucagon peptides disclosed herein. In addition applicants also believe that a truncated oxyntomodulin molecule comprising a glucagon peptide of the invention, having the terminal four amino acids of oxyntomodulin removed, will also be effective in suppressing appetite and inducing weight loss/weight maintenance.

Accordingly, the present invention also encompasses the modified glucagon peptides of the present invention that have a carboxy terminal extension of SEQ ID NO: 21 (KRNRN-NIA) or SEQ ID NO: 22. In accordance with one embodiment a glucagon agonist analog of SEQ ID NO: 33, further comprising the amino acid sequence of SEQ ID NO: 21 (KRN-RNNIA) or SEQ ID NO: 22 linked to amino acid 29 of the glucagon peptide, is administered to individuals to induce weight loss or prevent weight gain. In accordance with one embodiment a glucagon agonist analog of SEQ ID NO: 11 or SEQ ID NO: 13, further comprising the amino acid sequence of SEQ ID NO: 21 (KRNRNNIA) or SEQ ID NO: 22 linked to amino acid 29 of the glucagon peptide, is administered to individuals to induce weight loss or prevent weight gain. In another embodiment a method of reducing weight gain or inducing weight loss in an individual comprises administering an effective amount of a composition comprising a glucagon agonist comprising a glucagon peptide selected from the group consisting of SEQ ID NO: 2, SEQ ID NO: 3, SEQ ID NO: 4 or SEQ ID NO: 5, wherein amino acid 29 of the glucagon peptide is bound to a second peptide through a peptide bond, and said second peptide comprises the sequence of SEQ ID NO: 24 (KRNRNNIA) or SEQ ID NO: 25, and wherein a PEG chain of about 1,000 to 40,000 Daltons is covalently bound to an amino acid residue at position 21 and/or 24. In one embodiment the glucagon peptide segment of the glucagon agonist is selected from the group consisting of SEQ ID NO: 14, SEQ ID NO: 15, SEQ ID NO: 16, SEQ ID NO: 17, SEQ ID NO: 18 and SEQ ID NO: 19, wherein a PEG chain of about 1,000 to 40,000 Daltons is covalently bound to an amino acid residue at position 16, 17, 21 or 24.

Exendin-4, is a peptide made up of 39 amino acids. It is a powerful stimulator of a receptor known as GLP-1. This peptide has also been reported to suppress appetite and induce weight loss. Applicants have found that the terminal sequence of Exendin-4 when added at the carboxy terminus of glucagon improves the solubility and stability of glucagon without compromising the bioactivy of glucagon. In one embodiment the terminal ten amino acids of Exendin-4 (i.e. the sequence of SEQ ID NO: 20 (GPSSGAPPPS)) are linked to the carboxy terminus of a glucagon peptide of the present disclosure. These fusion proteins are anticipated to have pharmacological activity for suppressing appetite and inducing weight loss/weight maintenance. In one embodiment the terminal amino acid of the SEQ ID NO: 20 extension comprises an amide group in place of the carboxy group (i.e., SEQ ID NO: 23) and this sequence is linked to the carboxy terminus of a glucagon peptide of the present disclosure.

In one embodiment a method of reducing weight gain or inducing weight loss in an individual comprises administering an effective amount of a composition comprising a glucagon agonist comprising a glucagon peptide of SEQ ID NO: 33 wherein amino acid 29 of the glucagon peptide is bound to a second peptide through a peptide bond, and said second peptide comprises the sequence of SEQ ID NO: 20 (GPSS-GAPPPS) or SEQ ID NO: 23. In one embodiment the glucagon peptide is selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13 wherein amino acid 29 of the glucagon peptide is bound to a second peptide through a peptide bond, and said second peptide comprises the sequence of SEQ ID NO: 20 (GPSS-GAPPPS) or SEQ ID NO: 23. In one embodiment the glucagon peptide of the glucagon agonist is selected from the group consisting of SEQ ID NO: 11 and SEQ ID NO: 13. In one embodiment the glucagon peptide segment of the fusion peptide is selected from the group consisting of SEQ ID NO: 14, SEQ ID NO: 15, SEQ ID NO: 16 and SEQ ID NO: 17, wherein the molecular weight of the PEG chain is selected from the range of 500 to 40,000 Daltons. More particularly, in one embodiment the glucagon peptide of the fusion peptide is selected from the group consisting of SEQ ID NO: 16 and SEQ ID NO: 17 wherein the molecular weight of the PEG chain is selected from the range of 1,000 to 5,000.

In another embodiment a composition is administered to a patient to suppress appetite, prevent weight gain and/or induce weight loss by the administration of a pharmaceutical composition comprising a first pegylated glucagon peptide and a second pegylated glucagon peptide, wherein the first and second peptide are fusion peptides comprising a c-terminal peptide extension comprising SEQ ID NO: 20 (GPSS-GAPPPS) or SEQ ID NO: 23. The first pegylated glycogen peptide comprising a covalently linked PEG of about 500 to about 10,000 Daltons and the second pegylated glucagon peptide comprising a covalently linked PEG chain of about 10,000 to about 40,000 Daltons.

The present disclosure also encompasses multimers of the modified glucagon peptides disclosed herein. Two or more of the modified glucagon peptides can be linked together using standard linking agents and procedures known to those skilled in the art. For example, dimers can be formed between two modified glucagon peptides through the use of bifunctional thiol crosslinkers and bi-functional amine crosslinkers, particularly for the glucagon peptides that have been substituted with cysteine, lysine ornithine, homocysteine or acetyl phenylalanine residues (e.g. SEQ ID NO: 4 and SEQ ID NO: 5). The dimer can be a homodimer or alternatively can be a heterodimer. In one embodiment the dimer comprises a homodimer of a glucagon fusion peptide wherein the glucagon peptide portion comprises an agonist analog of SEQ ID NO: 11 and an amino acid sequence of SEQ ID NO: 20 (GPSSGAPPPS), SEQ ID NO: 21 (KRNRNNIA) or SEQ ID NO: 22 (KRNR) linked to amino acid 29 of the glucagon peptide. In another embodiment the dimer comprises a homodimer of a glucagon agonist analog of SEQ ID NO: 11, wherein the glucagon peptide further comprises a polyethylene glycol chain covalently bound to position 21 or 24 of the glucagon peptide.

In accordance with one embodiment a dimer is provided comprising a first glucagon peptide bound to a second glucagon peptide via a linker, wherein the first glucagon peptide comprises a peptide selected from the group consisting of SEQ ID NO: 1, SEQ ID NO: 7, SEQ ID NO: 8, SEQ ID NO: 9, SEQ ID NO: 10 and SEQ ID NO: 11 and the second glucagon peptide comprises SEQ ID NO: 33. Furthermore, with regards to the second glucagon peptide, when the amino acid at position 28 is asparagine and the amino acid at position 29 is threonine, the second glucagon peptide further comprises one to two amino acids (independently selected from the group consisting of Lys, Arg, His, Asp or Glu), added to the carboxy terminus of the second glucagon glucagon peptide, and pharmaceutically acceptable salts of said glucagon polypeptides.

In accordance with another embodiment a dimer is provided comprising a first glucagon peptide bound to a second glucagon peptide via a linker, wherein said first glucagon peptide is selected from the group consisting of SEQ ID NO: 2, SEQ ID NO: 3, SEQ ID NO: 4, SEQ ID NO: 5, SEQ ID NO: 8, SEQ ID NO: 9, SEQ ID NO: 10, SEQ ID NO: 11, SEQ ID NO: 12 and SEQ ID NO: 13 and the second glucagon peptide is independently selected from the group consisting of SEQ ID NO: 11 and SEQ ID NO: 13, and pharmaceutically acceptable salts of said glucagon polypeptides. In one embodiment the first glucagon peptide is selected from the group consisting of SEQ ID NO: 7 and the second glucagon peptide is independently selected from the group consisting of SEQ ID NO: 11, SEQ ID NO: 12 and SEQ ID NO: 13. In one embodiment the dimer is formed between two peptides wherein each peptide comprising the amino acid sequence of SEQ ID NO: 11.

In accordance with one embodiment a pharmaceutical composition is provided wherein the composition comprises a glucagon agonist analog of the present disclosure, or pharmaceutically acceptable salt thereof, and a pharmaceutically acceptable carrier. In one embodiment the pharmaceutical composition comprises a 1 mg/ml concentration of the glucagon agonist analog and 10-50 mM Triethanolamine at pH 7.0-8.5. In one embodiment the pharmaceutical composition comprises a 1 mg/ml concentration of the glucagon agonist analog and 20 mM Triethanolamine at pH 8.5.

The modified glucagon peptides of the present invention can be provided in accordance with one embodiment as part of a kit. In one embodiment a kit for administering a glucagon agonist to a patient in need thereof is provided wherein the kit comprises any of the glucagon peptides of the invention in aqueous solution. Exemplary glucagon peptides for inclusion in such kits include a glucagon peptide selected from the group consisting of 1) a glucagon peptide comprising the sequence of SEQ ID NO: 7, SEQ ID NO: 10, SEQ ID NO:11 or SEQ ID NO: 13 or SEQ ID NO: 33; 2) a glucagon fusion peptide comprising a glucagon agonist analog of SEQ ID NO: 11 or SEQ ID NO: 13 or SEQ ID NO: 33, and an amino acid sequence of SEQ ID NO: 20 (GPSSGAPPPS), SEQ ID NO: 21 (KRNRNNIA) or SEQ ID NO: 22 (KRNR) linked to amino acid 29 of the glucagon peptide; and 3) a pegylated glucagon peptide of SEQ ID NO: 11 or SEQ ID NO: 13 or SEQ ID NO: 33, further comprising an amino acid sequence of SEQ ID NO: 20 (GPSSGAPPPS), SEQ ID NO: 21 (KRNRNNIA) or SEQ ID NO: 22 (KRNR) linked to amino acid 29 of the glucagon peptide, wherein the PEG chain covalently bound to position 16, 17, 21 or 24 has a molecular weight of about 500 to about 40,000 Daltons. In one embodiment the kit is provided with a device for administering the glucagon composition to a patient, e.g. syringe needle, pen device, jet injector or other needle-free injector. The kit may alternatively or in addition include one or more of a variety of containers, e.g., vials, tubes, bottles, single or multi-chambered pre-filled syringes, cartridges, infusion pumps (external or implantable), jet injectors, pre-filled pen devices and the like, optionally containing the glucagon peptide. Preferably, the kits will also include instructions for use. In accordance with one embodiment the device of the kit is an aerosol dispensing device, wherein the composition is prepackaged within the aerosol device. In another embodiment the kit comprises a syringe and a needle, and in one embodiment the glucagon composition is prepackaged within the syringe.

The compounds of this invention may be prepared by standard synthetic methods, recombinant DNA techniques, or any other methods of preparing peptides and fusion proteins. Although certain non-natural amino acids cannot be expressed by standard recombinant DNA techniques, techniques for their preparation are known in the art. Compounds of this invention that encompass non-peptide portions may be synthesized by standard organic chemistry reactions, in addition to standard peptide chemistry reactions when applicable.

EXAMPLES

General Synthesis Protocol

Glucagon analogs were synthesized using HBTU-activated "Fast Boc" single coupling starting from 0.2 mmole of Boc Thr(OBzl)Pam resin on a modified Applied Biosystem 430A peptide synthesizer. Boc amino acids and HBTU were obtained from Midwest Biotech (Fishers, Ind.). Side chain protecting groups used were: Arg(Tos), Asn(Xan), Asp (OcHex), Cys(pMeBzl), His(Bom), Lys(2Cl—Z), Ser (OBzl), Thr(OBzl), Tyr(2Br—Z), and Trp(CHO). The sidechain protecting group on the N-terminal His was Boc.

Each completed peptidyl resin was treated with a solution of 20% piperidine in dimethylformamide to remove the formyl group from the tryptophan. Liquid hydrogen fluoride cleavages were performed in the presence of p-cresol and dimethyl sulfide. The cleavage was run for 1 hour in an ice bath using an HF apparatus (Pennisula Labs). After evaporation of the HF, the residue was suspended in diethyl ether and the solid materials were filtered. Each peptide was extracted into 30-70 ml aqueous acetic acid and a diluted aliquot was analyzed by HPLC [Beckman System Gold, 0.46×5 cm Zorbax C8, 1 ml/min, 45 C, 214 nm, A buffer=0.1% TFA, B=0.1% TFA/90% acetonitrile, gradient of 10% to 80% B over 10 min].

Purification was done on a FPLC over a 2.2×25 cm Kromasil C18 column while monitoring the UV at 214 nm and collecting 5 minute fractions. The homogeneous fractions were combined and lyophilized to give a product purity of >95%. The correct molecular mass and purity were confirmed using MALDI-mass spectral analysis.

General Pegylation Protocol: (Cys-Maleimido)

Typically, the glucagon Cys analog is dissolved in phosphate buffered saline (5-10 mg/ml) and 0.01M ethylenediamine tetraacetic acid is added (10-15% of total volume). Excess (2-fold) maleimido methoxyPEG reagent (Nektar) is added and the reaction stirred at room temp while monitoring reaction progress by HPLC. After 8-24 hrs, the reaction mixture, is acidified and loaded onto a preparative reverse phase column for purification using 0.1% TFA/acetonitrile gradient. The appropriate fractions were combined and lyophilized to give the desired pegylated analogs.

Example 1

Synthesis of Glucagon Cys[17] (1-29) and Similar MonoCys Analogs 0.2 mmole Boc Thr(OBzl) Pam resin (SynChem Inc) in a 60 ml reaction vessel and the following sequence was entered and run on a modified Applied Biosystems 430A Peptide Synthesizer using FastBoc HBTU-activated single couplings.

HSQGTFTSDYSKYLDSCRAQDFVQWLMNT    (SEQ ID NO: 27)

The following side chain protecting groups were used: Arg(Tos), Asp(OcHex), Asn(Xan), Cys(pMeBzl), Glu (OcHex), His(Boc), Lys(2Cl—Z), Ser(Bzl), Thr(Bzl), Trp (CHO), and Tyr(Br—Z). The completed peptidyl resin was treated with 20% piperidine/dimethylformamide to remove the Trp formyl protection then transferred to an HF reaction vessel and dried in vacuo. 1.0 ml p-cresol and 0.5 ml dimethyl sulfide were added along with a magnetic stir bar. The vessel was attached to the HF apparatus (Pennisula Labs), cooled in a dry ice/methanol bath, evacuated, and aprox. 10 ml liquid hydrogen fluoride was condensed in. The reaction was stirred in an ice bath for 1 hr then the HF was removed in vacuo. The residue was suspended in ethyl ether; the solids were filtered, washed with ether, and the peptide extracted into 50 ml aqueous acetic acid. An analytical HPLC was run [0.46×5 cm Zorbax C8, 1 ml/min, 45 C, 214 nm, A buffer of 0.1% TFA, B buffer of 0.1% TFA/90% ACN, gradient=10% B to 80% B over 10 min.] with a small sample of the cleavage extract. The remaining extract was loaded onto a 2.2×25 cm Kromasil C18 preparative reverse phase column and an acetonitrile gradient was run using a Pharmacia FPLC system. 5 min fractions were collected while monitoring the UV at 214 nm (2.0 A). A=0.1% TFA, B=0.1% TFA/50% acetonitrile. Gradient=30% B to 100% B over 450 min.

The fractions containing the purest product (48-52) were combined frozen, and lyophilized to give 30.1 mg. An HPLC analysis of the product demonstrated a purity of >90% and MALDI mass spectral analysis demonstrated the desired mass of 3429.7. Glucagon $Cys^{21}$, Glucagon $Cys^{24}$, and Glucagon $Cys^{29}$ were similarly prepared.

Example 2

Synthesis of Glucagon-Cex and Other C-Terminal Extended Analogs 285 mg (0.2 mmole) methoxybenzhydrylamine resin (Midwest Biotech) was placed in a 60 ml reaction vessel and the following sequence was entered and run on a modified Applied Biosystems 430A peptide synthesizer using FastBoc HBTU-activated single couplings.

HSQGTFTSDYSKYLDSRRAQDFVQWLMNTGPSSGAPPPS    (SEQ ID NO: 28)

The following side chain protecting groups were used: Arg(Tos), Asp(OcHex), Asn(Xan), Cys(pMeBzl), Glu (OcHex), His(Boc), Lys(2Cl—Z), Ser(Bzl), Thr(Bzl), Trp (CHO), and Tyr(Br—Z). The completed peptidyl resin was treated with 20% piperidine/dimethylformamide to remove the Trp formyl protection then transferred to HF reaction vessel and dried in vacuo. 1.0 ml p-cresol and 0.5 ml dimethyl sulfide were added along with a magnetic stir bar. The vessel was attached to the HF apparatus (Pennisula Labs), cooled in a dry ice/methanol bath, evacuated, and aprox. 10 ml liquid hydrogen fluoride was condensed in. The reaction was stirred in an ice bath for 1 hr then the HF was removed in vacuo. The residue was suspended in ethyl ether; the solids were filtered, washed with ether, and the peptide extracted into 50 ml aqueous acetic acid. An analytical HPLC was run [0.46×5 cm Zorbax C8, 1 ml/min, 45 C, 214 nm, A buffer of 0.1% TFA, B buffer of 0.1% TFA/90% ACN, gradient=10% B to 80% B over 10 min.] on an aliquot of the cleavage extract. The extract was loaded onto a 2.2×25 cm Kromasil C18 preparative reverse phase column and an acetonitrile gradient was run for elution using a Pharmacia FPLC system. 5 min fractions were collected while monitoring the UV at 214 nm (2.0 A). A=0.1% TFA, B=0.1% TFA/50% acetonitrile. Gradient=30% B to 100% B over 450 min. Fractions 58-65 were combined, frozen and lyophilized to give 198.1 mg.

HPLC analysis of the product showed a purity of greater than 95%. MALDI mass spectral analysis showed the presence of the desired theoretical mass of 4316.7 with the product as a C-terminal amide. Oxyntomodulin and oxyntomodulin-KRNR were similarly prepared as the C-terminal carboxylic acids starting with the appropriately loaded PAM-resin.

Example 3

Glucagon $Cys^{17}$ Mal-PEG-5K 15.1 mg of Glucagon $Cys^{17}$ (1-29) and 27.3 mg methoxy poly(ethyleneglycol) maleimide avg. M. W. 5000 (mPEG-Mal-5000, Nektar Therapeutics) were dissolved in 3.5 ml phosphate buffered saline (PBS) and 0.5 ml 0.01M ethylenediamine tetraacetic acid (EDTA) was added. The reaction was stirred at room temperature and the progress of the reaction was monitored by HPLC analysis [0.46×5 cm Zorbax C8, 1 ml/min, 45 C, 214 nm (0.5 A), A=0.1% TFA, B=0.1% TFA/ 90% ACN, gradient=10% B to 80% B over 10 min.].

After 5 hours, the reaction mixture was loaded onto 2.2×25 cm Kromasil C18 preparative reverse phase column. An acetonitrile gradient was run on a Pharmacia FPLC while monitoring the UV wavelength at 214 nm and collecting 5 min fractions. A=0.1% TFA, B=0.1% TFA/50% acetonitrile, gradient=30% B to 100% B over 450 min. The fractions corresponding to the product were combined, frozen and lyophilized to give 25.9 mg.

This product was analyzed on HPLC [0.46×5 cm Zorbax C8, 1 ml/min, 45 C, 214 nm (0.5 A), A=0.1% TFA, B=0.1% TFA/90% ACN, gradient=10% B to 80% B over 10 min.] which showed a purity of aprox. 90%. MALDI (matrix assisted laser desorption ionization) mass spectral analysis showed a broad mass range (typical of PEG derivatives) of 8700 to 9500. This shows an addition to the mass of the starting glucagon peptide (3429) of approximately 5,000 a.m.u.

Example 4

Glucagon $Cys^{21}$ Mal-PEG-5K 21.6 mg of Glucagon $Cys^{21}$ (1-29) and 24 mg mPEG-MAL-5000 (Nektar Therapeutics) were dissolved in 3.5 ml phosphate buffered saline (PBS) and 0.5 ml 0.01M ethylene diamine tetraacetic acid (EDTA) was added. The reaction was stirred at room temp. After 2 hrs, another 12.7 mg of mPEG-MAL-5000 was added. After 8 hrs, the reaction mixture was loaded onto a 2.2×25 cm Vydac C18 preparative reverse phase column and an acetonitrile gradient was run on a Pharmacia FPLC at 4 ml/min while collecting 5 min fractions. A=0.1% TFA, B=0.1% TFA/50% ACN. Gradient=20% to 80% B over 450 min.

The fractions corresponding to the appearance of product were combined frozen and lyophilized to give 34 mg. Analysis of the product by analytical HPLC [0.46×5 cm Zorbax C8, 1 ml/min, 45 C, 214 nm (0.5 A), A=0.1% TFA, B=0.1%

TFA/90% ACN, gradient=10% B to 80% B over 10 min.] showed a homogeneous product that was different than starting glucagon peptide. MALDI (matrix assisted laser desorption ionization) mass spectral analysis showed a broad mass range (typical of PEG analogs) of 8700 to 9700. This shows an addition to the mass of the starting glucagon peptide (3470) of approximately 5,000 a.m.u.

Example 5

Glucagon Cys[24] Mal-PEG-5K 20.1 mg Glucagon C[24] (1-29) and 39.5 mg mPEG-Mal-5000 (Nektar Therapeutics) were dissolved in 3.5 ml PBS with stirring and 0.5 ml 0.01M EDTA was added. The reaction was stirred at room temp for 7 hrs, then another 40 mg of mPEG-Mal-5000 was added. After approximately 15 hr, the reaction mixture was loaded onto a 2.2×25 cm Vydac C18 preparative reverse phase column and an acetonitrile gradient was run using a Pharmacia FPLC. 5 min. fractions were collected while monitoring the UV at 214 nm (2.0 A). A buffer=0.1% TFA, B buffer=0.1% TFA/50% ACN, gradient=30% B to 100% B over 450 min. The fractions corresponding to product were combined, frozen and lyophilized to give 45.8 mg. MALDI mass spectral analysis showed a typical PEG broad signal with a maximum at 9175.2 which is approximately 5,000 a.m.u. more than Glucagon C[24] (3457.8).

Example 6

Glucagon Cys[24] Mal-PEG-20K 25.7 mg of Glucagon Cys[24] (1-29) and 40.7 mg mPEG-Mal-20K (Nektar Therapeutics) were dissolved in 3.5 ml PBS with stirring at room temp. and 0.5 ml 0.01M EDTA was added. After 6 hrs, the ratio of starting material to product was aprox. 60:40 as determined by HPLC. Another 25.1 mg of mPEG-Mal-20K was added and the reaction allowed to stir another 16 hrs. The product ratio had not significantly improved, so the reaction mixture was loaded onto a 2.2×25 cm Kromasil C18 preparative reverse phase column and purified on a Pharmacia FPLC using a gradient of 30% B to 100% B over 450 min. A buffer=0.1% TFA, B buffer=0.1% TFA/50% ACN, flow=4 ml/min, and 5 min fractions were collected while monitoring the UV at 214 nm (2.0 A). The fractions containing homogeneous product were combined, frozen and lyophilized to give 25.7 mg. Purity as determined by analytical HPLC was ±90%. A MALDI mass spectral analysis showed a broad peak from 23,000 to 27,000 which is approximately 20,000 a.m.u. more than starting Glucagon C[24] (3457.8).

Example 7

Glucagon Cys[29] Mal-PEG-5K 20.0 mg of Glucagon Cys[29] (1-29) and 24.7 mg mPEG-Mal-5000 (Nektar Therapeutics) were dissolved in 3.5 ml PBS with stirring at room temperature and 0.5 ml 0.01M EDTA was added. After 4 hr, another 15.6 mg of mPEG-Mal-5000 was added to drive the reaction to completion. After 8 hrs, the reaction mixture was loaded onto a 2.2×25 cm Vydac C18 preparative reverse phase column and an acetonitrile gradient was run on a Pharmacia FPLC system. 5 min fractions were collected while monitoring the UV at 214 nm (2.0 A). A=0.1% TFA, B=0.1% TFA/50% ACN. Fractions 75-97 were combined frozen and lyophilized to give 40.0 mg of product that is different than recovered starting material on HPLC (fractions 58-63). Analysis of the product by analytical HPLC [0.46×5 cm Zorbax C8, 1 ml/min, 45 C, 214 nm (0.5 A), A=0.1% TFA, B=0.1% TFA/90% ACN, gradient=10% B to 80% B over 10 min.] showed a purity greater than 95%. MALDI mass spectral analysis showed the presence of a PEG component with a mass range of 8,000 to 10,000 (maximum at 9025.3) which is 5,540 a.m.u. greater than starting material (3484.8).

Example 8

Glucagon Cys[24] (2-butyrolactone)

To 24.7 mg of Glucagon Cys[24] (1-29) was added 4 ml 0.05M ammonium bicarbonate/50% acetonitrile and 5.5 ul of a solution of 2-bromo-4-hydroxybutyric acid-γ-lactone (100 ul in 900 ul acetonitrile). After 3 hrs of stirring at room temperature, another 105 ul of lactone solution was added to the reaction mixture which was stirred another 15 hrs. The reaction mixture was diluted to 10 ml with 10% aqueous acetic acid and was loaded onto a 2.2×25 cm Kromasil C18 preparative reverse phase column. An acetonitrile gradient (20% B to 80% B over 450 min) was run on a Pharmacia FPLC while collecting 5 min fractions and monitoring the UV at 214 nm (2.0 A). Flow=4 ml/min, A=0.1% TFA, B=0.1% TFA/50% ACN. Fractions 74-77 were combined frozen and lyophilized to give 7.5 mg. HPLC analysis showed a purity of 95% and MALDI mass spect analysis showed a mass of 3540.7 or 84 mass units more than starting material. This result consistent with the addition of a single butyrolactone moiety.

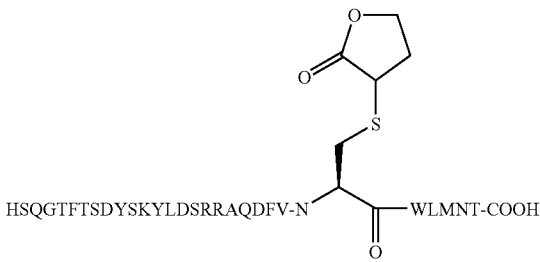

SEQ ID NO: 29
Molecular Weight = 3541.91
Exact Mass = 3538
Molecular Formula = C155H226N42O50S2

Example 9

Glucagon Cys[24] (S-carboxymethyl)

18.1 mg of Glucagon Cys[24] (1-29) was dissolved in 9.4 ml 0.1M sodium phosphate buffer (pH=9.2) and 0.6 ml bromoacetic acid solution (1.3 mg/ml in acetonitrile) was added. The reaction was stirred at room temperature and the reaction progress was followed by analytical HPLC. After 1 hr another 0.1 ml bromoacetic acid solution was added. The reaction was stirred another 60 min. then acidified with aqueous acetic acid and was loaded onto a 2.2×25 cm Kromasil C18 preparative reverse phase column for purification. An acetonitrile gradient was run on a Pharmacia FPLC (flow=4 ml/min) while collecting 5 min fractions and monitoring the UV at 214 nm (2.0 A). A=0.1% TFA, B=0.1% TFA/50% ACN. Fractions 26-29 were combined frozen and lyophilized to give several mg of product. Analytical HPLC showed a purity of 90% and MALDI mass spectral analysis confirmed a mass of 3515 for the desired product.

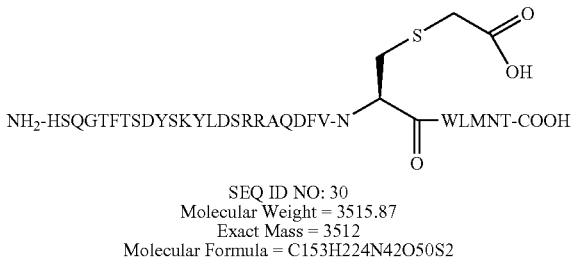

SEQ ID NO: 30
Molecular Weight = 3515.87
Exact Mass = 3512
Molecular Formula = C153H224N42O50S2

Example 10

Glucagon Cys$^{24}$ maleimido, PEG-3.4K-dimer 16 mg Glucagon Cys$^{24}$ and 1.02 mg Mal-PEG-Mal-3400, poly(ethyleneglycol)-bis-maleimide avg. M. W. 3400, (Nektar Therapeutics) were dissolved in 3.5 phosphate buffered saline and 0.5 ml 0.01M EDTA and the reaction was stirred at room temperature. After 16 hrs, another 16 mg of Glucagon Cys$^{24}$ was added and the stirring continued. After approximately 40 hrs, the reaction mixture was loaded onto a Pharmcia PepRPC 16/10 column and an acetonitrile gradient was run on a Pharmacia FPLC while collecting 2 min fractions and monitoring the UV at 214 nm (2.0 A). Flow=2 ml/min, A=0.1% TFA, B=0.1% TFA/50% ACN. Fractions 69-74 were combined frozen and lyophilized to give 10.4 mg. Analytical HPLC showed a purity of 90% and MALDI mass spectral analysis shows a component in the 9500-11,000 range which is consistent with the desired dimer.

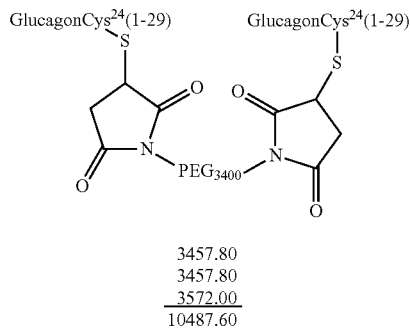

3457.80
3457.80
3572.00
10487.60

Example 11

Glucagon Solubility Assays

A solution (1 mg/ml or 3 mg/ml) of glucagon (or an analog) is prepared in 0.01N HCl. 100 ul of stock solution is diluted to 1 ml with 0.01N HCl and the UV absorbance (276 nm) is determined. The pH of the remaining stock solution is adjusted to pH7 using 200-250 ul 0.1M Na$_2$HPO$_4$ (pH9.2). The solution is allowed to stand overnight at 4° C. then centrifuged. 100 ul of supernatant is then diluted to 1 ml with 0.01N HCl, and the UV absorbance is determined (in duplicate).

The initial absorbance reading is compensated for the increase in volume and the following calculation is used to establish percent solubility:

$$\frac{\text{Final Absorbance}}{\text{Initial Absorbance}} \times 100 = \text{percent soluble}$$

Results are shown in Table 1 wherein Glucagon-Cex represents wild type glucagon (SEQ ID NO: 1) plus a carboxy terminal addition of SEQ ID NO: 20 and Glucagon-Cex R$^{12}$ represents SEQ ID NO: 1 wherein the Lys at position 12 is substituted with Arg and a peptide of SEQ ID NO: 20 is added to the carboxy terminus.

TABLE 1

Solubility date for glucagon analogs

| Analog | Percent Soluble |
| --- | --- |
| Glucagon | 16 |
| Glucagon-Cex, R12 | 104 |
| Glucagon-Cex | 87 |
| Oxyntomodulin | 104 |
| Glucagon, Cys17PEG5K | 94 |
| Glucagon, Cys21PEG5K | 105 |
| Glucagon, Cys24PEG5K | 133 |

The solubility the glucagon agonist analogs, D28, E29, E30, E15D28, D28E30, D28E29, was investigated using the same assay used for the compounds listed in Table 1. The data (shown in FIGS. 3 & 4) demonstrates the superior solubility of the D28, E29, E30, E15D28, D28E30, D28E29 analogs relative to native glucagon at pH values of 5.5 and 7.0. The data presented in FIG. 3 represents the solubility measured after 60 hours at 25° C., whereas the data presented in FIG. 4 represents the solubility measured after 24 hours at 25° C. and then 24 hours at 4° C. FIG. 5 represents data regarding the maximum solubility of the glucagon analogs D28, D28E30 and E15D28.

Example 12

Glucagon Receptor Binding Assay

The affinity of peptides to the glucagon receptor was measured in a competition binding assay utilizing scintillation proximity assay technology. Serial 3-fold dilutions of the peptides made in scintillation proximity assay buffer (0.05 M Tris-HCl, pH 7.5, 0.15 M NaCl, 0.1% w/v bovine serum albumin) were mixed in 96 well white/clear bottom plate (Corning Inc., Acton, Mass.) with 0.05 nM (3-[$^{125}$I]-iodotyrosyl) Tyr 10 glucagon (Amersham Biosciences, Piscataway, N.J.), 1-6 micrograms per well, plasma membrane fragments prepared from cells over-expressing human glucagon receptor, and 1 mg/well polyethyleneimine-treated wheat germ agglutinin type A scintillation proximity assay beads (Amersham Biosciences, Piscataway, N.J.). Upon 5 min shaking at 800 rpm on a rotary shaker, the plate was incubated 12 h at room temperature and then read on MicroBeta 1450 liquid scintillation counter (Perkin-Elmer, Wellesley, Mass.). Non-specifically bound (NSB) radioactivity was measured in the wells with 4 times greater concentration of "cold" native ligand than the highest concentration in test samples and total bound radioactivity was detected in the wells with no competitor. Percent specific binding was calculated as following:
% Specific Binding=((Bound-NSB)/(Total bound-NSB))×

100. IC$_{50}$ values were determined by using Origin software (OriginLab, Northampton, Mass.).

Example 13

Functional Assay-cAMP Synthesis

The ability of glucagon analogs to induce cAMP was measured in a firefly luciferase-based reporter assay. HEK293 cells co-transfected with either glucagon- or GLP-1 receptor and luciferase gene linked to cAMP responsive element were serum deprived by culturing 16 h in DMEM (Invitrogen, Carlsbad, Calif.) supplemented with 0.25% Bovine Growth Serum (HyClone, Logan, Utah) and then incubated with serial dilutions of either glucagon, GLP-1 or novel glucagon analogs for 5 h at 37° C., 5% CO$_2$ in 96 well poly-D-Lysine-coated "Biocoat" plates (BD Biosciences, San Jose, Calif.). At the end of the incubation 100 microliters of LucLite luminescence substrate reagent (Perkin-Elmer, Wellesley, Mass.) were added to each well. The plate was shaken briefly, incubated 10 min in the dark and light output was measured on MicroBeta-1450 liquid scintillation counter (Perkin-Elmer, Wellesley, Mass.). Effective 50% concentrations were calculated by using Origin software (OriginLab, Northampton, Mass. Results are shown in Tables 2 and 3.

TABLE 2 cAMP Induction by Glucagon Analogs with C-Terminus Extension

| Peptide | cAMP Induction | | | |
|---|---|---|---|---|
| | Glucagon Receptor | | GLP-1 Receptor | |
| | EC$_{50}$, nM | N* | EC$_{50}$, nM | N |
| Glucagon | 0.22 ± 0.09 | 14 | 3.85 ± 1.64 | 10 |
| GLP-1 | 2214.00 ± 182.43 | 2 | 0.04 ± 0.01 | 14 |
| Glucagon Cex | 0.25 ± 0.15 | 6 | 2.75 ± 2.03 | 7 |
| Oxyntomodulin | 3.25 ± 1.65 | 5 | 2.53 ± 1.74 | 5 |
| Oxyntomodulin KRNR | 2.77 ± 1.74 | 4 | 3.21 ± 0.49 | 2 |
| Glucagon R12 | 0.41 ± 0.17 | 6 | 0.48 ± 0.11 | 5 |
| Glucagon R12 Cex | 0.35 ± 0.23 | 10 | 1.25 ± 0.63 | 10 |
| Glucagon R12 K20 | 0.84 ± 0.40 | 5 | 0.82 ± 0.49 | 5 |
| Glucagon R12 K24 | 1.00 ± 0.39 | 4 | 1.25 ± 0.97 | 5 |
| Glucagon R12 K29 | 0.81 ± 0.49 | 5 | 0.41 ± 0.24 | 6 |
| Glucagon Amide | 0.26 ± 0.15 | 3 | 1.90 ± 0.35 | 2 |
| Oxyntomodulin C24 | 2.54 ± 0.63 | 2 | 5.27 ± 0.26 | 2 |
| Oxyntomodulin C24 PEG 20K | 0.97 ± 0.04 | 1 | 1.29 ± 0.11 | 1 |

*number of experiments

TABLE 3 cAMP Induction by Pegylated Glucagon Analogs

| Peptide | cAMP Induction | | | |
|---|---|---|---|---|
| | Glucagon Receptor | | GLP-1 Receptor | |
| | EC$_{50}$, nM | N* | EC$_{50}$, nM | N |
| Glucagon | 0.33 ± 0.23 | 18 | 12.71 ± 3.74 | 2 |
| Glucagon C17 PEG 5K | 0.82 ± 0.15 | 4 | 55.86 ± 1.13 | 2 |
| Glucagon C21 PEG 5K | 0.37 ± 0.16 | 6 | 11.52 ± 3.68 | 2 |
| Glucagon C24 PEG 5K | 0.22 ± 0.10 | 12 | 13.65 ± 2.95 | 4 |
| Glucagon C29 PEG 5K | 0.96 ± 0.07 | 2 | 12.71 ± 3.74 | 2 |
| Glucagon C24 PEG 20K | 0.08 ± 0.05 | 3 | Not determined | |
| Glucagon C24 Dimer | 0.10 ± 0.05 | 3 | Not determined | |
| GLP-1 | >1000 | | 0.05 ± 0.02 | 4 |

*number of experiments

Data for additional glucagon analogs is presented in FIGS. 6-9 and in Table 4

TABLE 4

Observed EC50s (nM) in Cells Overexpressing the Glucagon Receptor

| | Test 1 | Test 2 | Test 3 | Test 4 |
|---|---|---|---|---|
| Glucagon standard | 0.12 | 0.04 | 0.05 | 0.11 |
| K29 | 0.35 | | | 0.22 |
| K30 | 0.22 | 0.06 | | |
| K29, K30 | 0.89 | | | |
| K30, K31 | | 0.12 | | |
| D28 | | 0.05 | | 0.17 |
| E28 | | | 0.14 | |
| E29 | | 0.05 | 0.04 | |
| E30 | | 0.04 | | |
| D28, E29 | | | 0.03 | |
| D28, E30 | | | 0.05 | |
| D28, E15 | | | 0.15 | |

Example 14

Stability Assay for Glucagon Cys-Maleimido PEG Analogs

Each glucagon analog was dissolved in water or PBS and an initial HPLC analysis was conducted. After adjusting the pH (4, 5, 6, 7), the samples were incubated over a specified time period at 37° C. and re-analyzed by HPLC to determine the integrity of the peptide. The concentration of the specific peptide of interest was determined and the percent remaining intact was calculated relative to the initial analysis. Results for Glucagon Cys$^{21}$-maleimidoPEG$_{5K}$ are shown in FIGS. 1 and 2.

Example 15

Changes in Serum Glucose Concentration in Beagle Dogs after Administration of Glucagon Analogs Canine/Beagle dogs of 8-12 kg, being of 8-16 months of age and good health were used to determine the pharmacokinetics and pharmacodynamics of glucagon action. Every animal was fasted overnight and bled at the following time points after each dose: 0 hr. (pre-dose), 5, 10, 20, 30, 45, 60, 90, 120, 240 minutes post dose. Six animals were used for each dose group and approximately 1-2 ml of whole blood was withdrawn at each time point. About 1.0 ml whole blood was added to K$_2$ EDTA tubes containing a sufficient volume of Trasylol (aprotinin) to yield at least 500 KIU/mL of whole blood. Approximately 500 uL plasma was collected after centrifuging the samples in a refrigerated centrifuge at about 1,500-3,000×g for 10-15 min. The samples were transferred to plastic vials and stored frozen at −70° C., or below. The remaining 1.0 mL of whole blood was converted into serum by placing blood sample into an empty tube, letting sit at ambient temperature for 15-20 min, then centrifuging at 1,500-3,000×g for 10-15 min. in a refrigerated centrifuge. The samples were transferred to plastic vials and stored frozen at −70° C., or below. Glucagon and the analogs were dissolved in 0.01N HCl at a concentration of 0.1667 mg/ml and the animals were dosed at 0.03 ml/kg.

The animals were administered a 0.005 mg/kg dose intramuscularly of either glucagon, a glucagon analog comprising glucagon with the sequence of SEQ ID NO: 31 linked to the carboxy terminus of glucagon (glucagon-CEX) or a glucagon analog comprising an aspartic acid substitution at amino acid 28 (glucagon-Asp28) SEQ ID NO: 11. The resulting data is presented in FIG. 10.

The invention claimed is:

1. A glucagon peptide with improved solubility relative to native glucagon (SEQ ID NO: 1), that is an analog of SEQ ID NO: 1 comprising (a) one, two, or three charged amino acid(s) C-terminal to the amino acid at position 27 of the glucagon peptide, (b) a Leu or Nle at position 27, and (c) up to 4 additional amino acid modifications relative to SEQ ID NO: 1, wherein the glucagon peptide retains improved solubility and glucagon activity.

2. The glucagon peptide of claim 1, wherein said one, two, or three charged amino acid are negatively charged amino acids.

3. The glucagon peptide of claim 2, wherein the negatively charged amino acids are selected from the group consisting of Glu and Asp.

4. The glucagon peptide of claim 3, wherein (i) the amino acid at position 28 is Asp, or (ii) the amino acid at position 29 is Glu, or both (i) and (ii).

5. The glucagon peptide of claim 4, wherein the additional amino acid modifications are:
   amino acid substitutions at positions 1, 2, 5, 7, 10, 11, 12, 13, 14, 16, 17, 18, 19, 20, 21, and 24 relative to SEQ ID NO: 1.

6. A homo dimer comprising two glucagon peptides of claim 5 bound to one another through a linker.

7. The glucagon peptide of claim 2, wherein two or more charged amino acids C-terminal to the amino acid at position 27 are negatively charged.

8. The glucagon peptide of claim 7, comprising
   a. a substitution of the amino acid at position 15 with Glu, homo-Glu, cysteic acid, homo cysteic acid;
   b. a hydrophilic moiety covalently bound at position 16, 17, 20, 21, 24 or 29 of said glucagon peptide;
   c. a sequence selected from the group consisting of SEQ ID NO: 20, SEQ ID NO: 21, and SEQ ID NO: 22 bound to the carboxy terminus of said glucagon peptide;
   d. an amino acid at position 2 selected from the group consisting of d-serine, alanine, glycine, n-methyl serine and amino isobutyric acid; or the amino acid at position 1 is selected from the group consisting of dhistidine, desaminohistidine, hydroxyl-histidine, acetyl-histidine and homo-histidine; or
   e. a combination thereof.

9. A glucagon peptide with improved solubility relative to native glucagon (SEQ ID NO: 1) comprising the sequence of SEQ ID NO: 33 or an analog of SEQ ID NO: 33, wherein said analog differs from SEQ ID NO: 33 by one to three amino acid substitutions, said amino acid substitutions located at one or more positions selected from positions 1, 2, 5, 7, 10, 11, 12, 13, 14, 16, 17, 18, 19, 20, 21 and 24 of the analog, with the proviso that said glucagon peptide comprises a charged amino acid at position 28 or 29, or an additional acidic amino acid added to the carboxy terminus of the peptide.

10. The glucagon peptide of claim 1 wherein the glucagon peptide comprises the sequence of any one of SEQ ID NOs: 7, 8, 9, 11, 12, 13, 32, 33, 34, or 38.

11. A pharmaceutical composition comprising the glucagon peptide of claim 5, 9, or 7 or a pharmaceutically acceptable salt thereof; and a pharmaceutically acceptable carrier.

12. The glucagon peptide of claim 9 further comprising a hydrophilic moiety covalently bound at position 16, 17, 21 or 24 of the glucagon peptide.

13. The glucagon peptide of claim 12 wherein the hydrophilic moiety is polyethylene glycol (PEG).

14. The glucagon peptide of claim 13 wherein the glucagon peptide further comprises a sequence selected from the group consisting of SEQ ID NO: 20, SEQ ID NO: 21, and SEQ ID NO: 22 bound to the carboxy terminus of said glucagon peptide.

15. A solution comprising the glucagon peptide of claim 1, 5, or 9 or a pharmaceutically acceptable salt thereof; and a pharmaceutically acceptable carrier; said solution at pH of about 5.5 to about 8.0.

16. A kit for administering a glucagon agonist to a patient in need thereof, said kit comprising the solution of claim 15; and a device for administering said composition to a patient.

17. The kit of claim 16 wherein said device:
   is an aerosol dispensing device, wherein the composition is prepackaged within the aerosol device; or
   comprises a syringe and a needle, wherein the composition is prepackaged within the syringe.

18. A method of treating hypoglycemia in a patient, comprising administering to the patient the glucagon peptide of claim 1, 5, or 9 in an amount effective for treating hypoglycemia.

* * * * *

UNITED STATES PATENT AND TRADEMARK OFFICE
CERTIFICATE OF CORRECTION

PATENT NO.         : 8,669,228 B2                                                    Page 1 of 1
APPLICATION NO.    : 12/522129
DATED              : March 11, 2014
INVENTOR(S)        : Dimarchi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 646 days.

Signed and Sealed this
Twelfth Day of May, 2015

Michelle K. Lee
*Director of the United States Patent and Trademark Office*